(12) United States Patent
Harding et al.

(10) Patent No.: US 8,455,191 B2
(45) Date of Patent: Jun. 4, 2013

(54) CELL TRANSDIFFERENTIATION INTO BROWN ADIPOCYTES

(75) Inventors: Paul A. Harding, Oxford, OH (US); Zhenqing Zhou, Oxford, OH (US)

(73) Assignee: Miami University, Oxford, OH (US)

( * ) Notice: Subject to any disclaimer, the term of this patent is extended or adjusted under 35 U.S.C. 154(b) by 0 days.

(21) Appl. No.: 12/871,209

(22) Filed: Aug. 30, 2010

(65) Prior Publication Data

US 2011/0060034 A1    Mar. 10, 2011

Related U.S. Application Data

(60) Provisional application No. 61/237,787, filed on Aug. 28, 2009.

(51) Int. Cl.
*C12Q 1/68*      (2006.01)
*A61K 48/00*    (2006.01)
*C07H 21/02*   (2006.01)

(52) U.S. Cl.
USPC ........... 435/6.1; 435/325; 435/375; 514/44 R; 536/23.1

(58) Field of Classification Search
None
See application file for complete search history.

(56) References Cited

U.S. PATENT DOCUMENTS

| | | |
|---|---|---|
| 5,399,346 A | 3/1995 | Anderson et al. |
| 2006/0160218 A1 | 7/2006 | Slack et al. |
| 2008/0090257 A1 | 4/2008 | Li |

OTHER PUBLICATIONS

Flotte J. Cell. Physiol., 2007; 213:301-305.*
Gregoire et al., "Understanding Adipocyte Differentiation," Physiol. Rev. 78, p. 783-809 (1998).
Lilla et al., "Metelloproteases and Adipogenesis: A Weighty Subject," Am J Pathol. 160, p. 1551-4 (2002).
Kawaguchi et al., "ADAM 12 Protease Induces Adipogenesis in Transgenic Mice," Am. J. Path., 160, p. 1895-1903 (2002).
Higashiyama et al., "ADAM-mediated ectodomain shedding of HB-EGF in receptor cross-talk," Biochim Biophys Acta., 1751, p. 110-7 (2005).
Zhou et al., "Role of c-Fos/JunD in protecting stress-induced cell death," Cell Prolif., 40, p. 213-30 (2007).
Casteilla et al., "Virus-based Gene Transfer Approaches and Adipose Tissue Biology," Current Gene Therapy, 8, p. 79-87 (2008).
Claudio et al., "The RB2/p130 Gene: The Latest Weapon in the War against Lung Cancer?" Clin. Canc. Res. 6, p. 754-764 (2000).
Valet et al., "Understanding adipose tissue development from transgenic animal models," J. Lipid Res. 43, 835-60 (2002).
Nanba et al., "Dual intracellular signaling by proteolytic cleavage of membrane-anchored heparin-binding EGF-like growth factor," Cytokine Growth Factor Rev., 15, 15-19 (2004).
Nanba et al., "Proteolytic release of the carboxy-terminal fragment of proHB-EGF causes nuclear export of PLZF," J. Cell Biol., 163, 489-502 (2003).
Nakagawa et al., "Amino-terminal Processing of Cell Surface Heparin-binding Epidermal Growth Factor-like Growth Factor Up-regulates Its Juxtacrine but Not Its Paracrine Growth Factor Actvity," J Biol Chem., 271, 30858-63 (1996).
Asakura et al., "Cardiac hypertrophy is inhibited by antagonism of ADAM12 processing of HB-EGF: metalloproteinase inhibitors as a new therapy," Nat. Med., 8, 35-40 (2002).
Darwal, M and Harding, P., "Redirected Fibroblasts into Fat," Poster Abstract CB-12, Sigma Xi 2007 Annual Meeting & Student Research Conference, Nov. 2-3, 2007.
Darwal et al., "HB-EGF dependent stimulation of adipogenesis by ADAM 12S," Late Abstracts, 2762, The American Sociaty for Cell Biology 47th annual meeting, Dec. 1-5, 2007.

* cited by examiner

*Primary Examiner* — Doug Schultz
(74) *Attorney, Agent, or Firm* — Calfee, Halter & Griswold

(57) ABSTRACT

A method for converting animal cells into brown adipose tissue cells is provided that includes transforming the animal cells using an expression vector. The expression vector includes a nucleotide sequence encoding HB-EGF operatively linked to a promoter and a nucleotide sequence encoding ADAM 12 operatively linked to a promoter. Converting animal cells to brown adipose tissue cells can be used to treat obesity or to treat cancer by converting target cells to brown adipose tissue cells.

9 Claims, 8 Drawing Sheets

Human HB-EGF amino acid sequence (SEQ ID NO: 1)
1
MKLLPSVVLKLFLAAVLSALVTGESLERLRRGLAAGTSNPDPPTVSTDQLLPLGGGRDRKVRDLQEADLDL
LRVTLSSKPQALATPNKEEHGKRKKKGKGLGKKRDPCLRKYKDFCIHGECKYVKELRAPSCICHPGYHGER
CHGLSLPVENRLYTYDHTTILAVVAVVLSSVCLLVIVGLLMFRYHRRGGYDVENEEKVKLGMTNSH
                                                                  208

FIG. 2A

Human HB-EGF cDNA nucleotide sequence (SEQ ID NO: 3)

1                                                                  60
atgaagctgc tgccgtcggt ggtgctgaag ctctttctgg ctgcagttct ctcggcactg
gtgactggcg agagcctgga gcggcttcgg agagggctag ctgctggaac cagcaacccg
gaccctccca ctgtatccac ggaccagctg ctaccccctag gaggcggccg ggaccggaaa
gtccgtgact gcaagaggc agatctggac cttttgagag tcactttatc ctccaagcca
caagcactgg ccacaccaaa caaggaggag cacgggaaaa gaaagaagaa aggcaagggg
ctagggaaga gagggaccc atgtcttcgg aaatacaagg acttctgcat ccatggagaa
tgcaaatatg tgaaggagct ccgggctccc tcctgcatct gccacccggg ttaccatgga
gagaggtgtc atgggctgag cctcccagtg gaaaatcgct tatataccta tgaccacaca
accatcctgg ccgtggtggc tgtggtgctg tcatctgtct gtctgctggt catcgtgggg
cttctcatgt ttaggtacca taggagagga ggttatgatg tggaaaatga agagaaagtg
aagttgggca tgactaattc ccactga
                           627

FIG. 2B

Human ADAM 12S amino acid sequence (SEQ ID NO: 2)

1                                                           59
MAARPLPVSPARALLLALAGALLAPCEARGVSLWNQGRADEVVSASVGSGDLWIPVKSF
DSKNHPEVLNIRLQRESKELIINLERNEGLIASSFTETHYLQDGTDVSLARNYTGHCYY
HGHVRGYSDSAVSLSTCSGLRGLIVFENESYVLEPMKSATNRYKLFPAKKLKSVRGSCG
SHHNTPNLAAKNVFPPPSQTWARRHKRETLKATKYVELVIVADNREFQRQGKDLEKVKQ
RLIEIANHVDKFYRPLNIRIVLVGVEVWNDMDKCSVSQDPFTSLHEFLDWRKMKLLPRK
SHDNAQLVSGVYFQGTTIGMAPIMSMCTADQSGGIVMDHSDNPLGAAVTLAHELGHNFG
MNHDTLDRGCSCQMAVEKGGCIMNASTGYPFPMVFSSCSRKDLETSLEKGMGVCLFNLP
EVRESFGGQKCGNRFVEEGEECDCGEPEECMNRCCNATTCTLKPDAVCAHGLCCEDCQL
KPAGTACRDSSNSCDLPEFCTGASPHCPANVYLHDGHSCQDVDGYCYNGICQTHEQQCV
TLWGPGAKPAPGICFERVNSAGDPYGNCGKVSKSSFAKCEMRDAKCGKIQCQGGASRPV
IGTNAVSIETNIPLQQGGRILCRGTHVYLGDDMPDPGLVLAGTKCADGKICLNRQCQNI
SVFGVHECAMQCHGRGVCNNRKNCHCEAHWAPPFCDKFGFGGSTDSGPIRQAEARQEAA
ESNRERGQGQEPVGSQEHASTASLTLI
                                                           735

FIG. 3

Human ADAM 12S cDNA nucleotide sequence (SEQ ID NO: 4)

```
1                                                            60
atggcagcgc gcccgctgcc cgtgtccccc gcccgcgccc tcctgctcgc cctggccggt
gctctgctcg cgccctgcga ggcccgaggg gtgagcttat ggaaccaagg aagagctgat
gaagttgtca gtgcctctgt tgggagtggg gacctctgga tcccagtgaa gagcttcgac
tccaagaatc atccagaagt gctgaatatt cgactacaac gggaaagcaa agaactgatc
ataaatctgg aaagaaatga aggtctcatt gccagcagtt tcacggaaac ccactatctg
caagacggta ctgatgtctc cctcgctcga aattacacgg tcactgtta  ctaccatgga
catgtacggg gatattctga ttcagcagtc agtctcagca cgtgttctgg tctcagggga
cttattgtgt ttgaaaatga aagctatgtc ttagaaccaa tgaaaagtgc aaccaacaga
tacaaaactct tcccagcgaa gaagctgaaa agcgtccggg gatcatgtgg atcacatcac
aacacaccaa acctcgctgc aaagaatgtg tttccaccac cctctcagac atgggcaaga
aggcataaaa gagagaccct caaggcaact aagtatgtgg agctggtgat cgtggcagac
aaccgagagt ttcagaggca aggaaaagat ctggaaaaag ttaagcagcg attaatagag
attgctaatc acgttgacaa gttttacaga ccactgaaca ttcggatcgt gttggtaggc
gtggaagtgt ggaatgacat ggacaaatgc tctgtaagtc aggacccatt caccagcctc
catgaatttc tggactggag gaagatgaag cttctacctc gcaaatccca tgacaatgcg
cagcttgtca gtggggttta tttccaaggg accaccatcg gcatggcccc aatcatgagc
atgtgcacgg cagaccagtc tgggggaatt gtcatggacc attcagacaa tcccttggt
gcagccgtga ccctggcaca tgagctgggc cacaatttcg gatgaatca  tgacacactg
gacagggct  gtagctgtca aatggcggtt gagaaggag  gctgcatcat gaacgcttcc
accgggtacc catttcccat ggtgttcagc agttgcagca ggaaggactt ggagaccagc
ctggagaaag aatgggggt  gtgcctgttt aacctgccgg aagtcaggga gtctttcggg
ggccagaagt gtgggaacag atttgtggaa gaggagagg  agtgtgactg tggggagcca
gaggaatgta tgaatcgctg ctgcaatgcc accacctgta ccctgaagcc ggacgctgtg
tgcgcacatg gctgtgctg  tgaagactgc cagctgaagc ctgcaggaac agcgtgcagg
gactccagca actcctgtga cctcccagag ttctgcacag gggccagccc tcactgccca
gccaacgtgt acctgcacga tgggcactca tgtcaggatg tggacggcta ctgctacaat
ggcatctgcc agactcacga gcagcagtgt gtcacgctct ggggaccagg tgctaaacct
gcccctggga tctgctttga gagagtcaat tctgcaggtg atccttatgg caactgtggc
aaagtctcga agagttcctt tgccaaatgc gagatgagag atgctaaatg tggaaaaatc
cagtgtcaag gaggtgccag ccggccagtc attggtacca atgccgtttc catagaaaca
aacatccccc tgcagcaagg aggccggatt ctgtgccggg gacccacgt  gtacttgggc
gatgacatgc cggacccagg gcttgtgctt gcaggcacaa agtgtgcaga tggaaaaatc
tgcctgaatc gtcaatgtca aaatattagt gtctttgggg ttcacgagtg tgcaatgcag
tgccacggca gaggggtgtg caacaacagg aagaactgcc actgcgaggc ccactgggca
cctcccttct gtgacaagtt tggcttttga ggaagcacag acagcggccc catccggcaa
gcagaagcaa ggcaggaagc tgcagagtcc aacagggagc gcggccaggg ccaggagccc
gtgggatcgc aggagcatgc gtctactgcc tcactgacac tcatctga
                                                           2208
```

FIG. 4

White Adipose Tissue Gene Expression
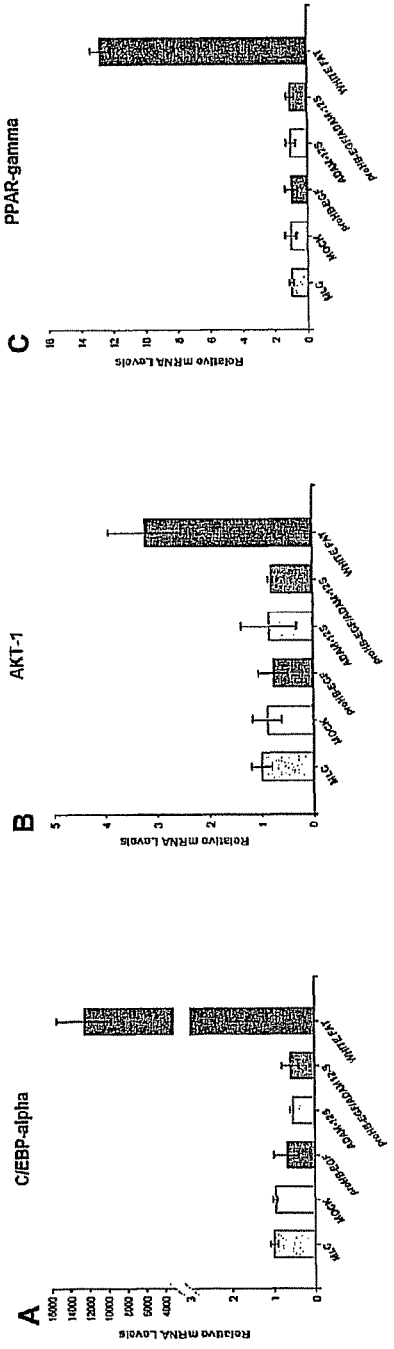
Brown Adipose Tissue Gene Expression
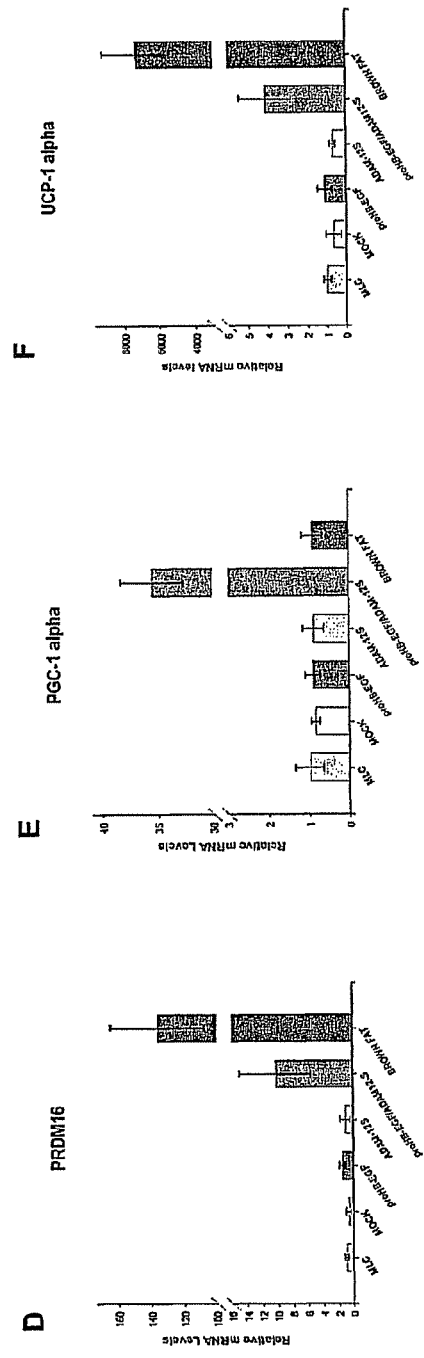
FIG. 8

SEQUENCE LISTING

<160> NUMBER OF SEQ ID NOS: 26

<210> SEQ ID NO 1
<211> LENGTH: 208
<212> TYPE: PRT
<213> ORGANISM: Homo sapiens

<400> SEQUENCE: 1

```
Met Lys Leu Leu Pro Ser Val Val Leu Lys Leu Phe Leu Ala Ala Val
1               5                   10                  15

Leu Ser Ala Leu Val Thr Gly Glu Ser Leu Glu Arg Leu Arg Arg Gly
                20                  25                  30

Leu Ala Ala Gly Thr Ser Asn Pro Asp Pro Pro Thr Val Ser Thr Asp
            35                  40                  45

Gln Leu Leu Pro Leu Gly Gly Gly Arg Asp Arg Lys Val Arg Asp Leu
        50                  55                  60

Gln Glu Ala Asp Leu Asp Leu Leu Arg Val Thr Leu Ser Ser Lys Pro
65                  70                  75                  80

Gln Ala Leu Ala Thr Pro Asn Lys Glu Glu His Gly Lys Arg Lys Lys
                85                  90                  95

Lys Gly Lys Gly Leu Gly Lys Lys Arg Asp Pro Cys Leu Arg Lys Tyr
                100                 105                 110

Lys Asp Phe Cys Ile His Gly Glu Cys Lys Tyr Val Lys Glu Leu Arg
            115                 120                 125

Ala Pro Ser Cys Ile Cys His Pro Gly Tyr His Gly Glu Arg Cys His
        130                 135                 140

Gly Leu Ser Leu Pro Val Glu Asn Arg Leu Tyr Thr Tyr Asp His Thr
145                 150                 155                 160

Thr Ile Leu Ala Val Val Ala Val Val Leu Ser Ser Val Cys Leu Leu
                165                 170                 175

Val Ile Val Gly Leu Leu Met Phe Arg Tyr His Arg Arg Gly Gly Tyr
                180                 185                 190

Asp Val Glu Asn Glu Glu Lys Val Lys Leu Gly Met Thr Asn Ser His
            195                 200                 205
```

<210> SEQ ID NO 2
<211> LENGTH: 735
<212> TYPE: PRT
<213> ORGANISM: Homo sapiens

<400> SEQUENCE: 2

-continued

```
Met Ala Ala Arg Pro Leu Pro Val Ser Pro Ala Arg Ala Leu Leu Leu
 1               5                  10                 15

Ala Leu Ala Gly Ala Leu Leu Ala Pro Cys Glu Ala Arg Gly Val Ser
            20                  25                 30

Leu Trp Asn Gln Gly Arg Ala Asp Glu Val Val Ser Ala Ser Val Gly
        35                  40                  45

Ser Gly Asp Leu Trp Ile Pro Val Lys Ser Phe Asp Ser Lys Asn His
 50                  55                  60

Pro Glu Val Leu Asn Ile Arg Leu Gln Arg Glu Ser Lys Glu Leu Ile
 65                  70                  75                  80

Ile Asn Leu Glu Arg Asn Glu Gly Leu Ile Ala Ser Ser Phe Thr Glu
                85                  90                  95

Thr His Tyr Leu Gln Asp Gly Thr Asp Val Ser Leu Ala Arg Asn Tyr
            100                 105                 110

Thr Gly His Cys Tyr Tyr His Gly His Val Arg Gly Tyr Ser Asp Ser
            115                 120                 125

Ala Val Ser Leu Ser Thr Cys Ser Gly Leu Arg Gly Leu Ile Val Phe
    130                 135                 140

Glu Asn Glu Ser Tyr Val Leu Glu Pro Met Lys Ser Ala Thr Asn Arg
145                 150                 155                 160

Tyr Lys Leu Phe Pro Ala Lys Lys Leu Lys Ser Val Arg Gly Ser Cys
                165                 170                 175

Gly Ser His His Asn Thr Pro Asn Leu Ala Ala Lys Asn Val Phe Pro
            180                 185                 190

Pro Pro Ser Gln Thr Trp Ala Arg Arg His Lys Arg Glu Thr Leu Lys
        195                 200                 205

Ala Thr Lys Tyr Val Glu Leu Val Ile Val Ala Asp Asn Arg Glu Phe
210                 215                 220

Gln Arg Gln Gly Lys Asp Leu Glu Lys Val Lys Gln Arg Leu Ile Glu
225                 230                 235                 240

Ile Ala Asn His Val Asp Lys Phe Tyr Arg Pro Leu Asn Ile Arg Ile
                245                 250                 255

Val Leu Val Gly Val Glu Val Trp Asn Asp Met Asp Lys Cys Ser Val
            260                 265                 270

Ser Gln Asp Pro Phe Thr Ser Leu His Glu Phe Leu Asp Trp Arg Lys
        275                 280                 285

Met Lys Leu Leu Pro Arg Lys Ser His Asp Asn Ala Gln Leu Val Ser
290                 295                 300

Gly Val Tyr Phe Gln Gly Thr Thr Ile Gly Met Ala Pro Ile Met Ser
305                 310                 315                 320

Met Cys Thr Ala Asp Gln Ser Gly Gly Ile Val Met Asp His Ser Asp
                325                 330                 335

Asn Pro Leu Gly Ala Ala Val Thr Leu Ala His Glu Leu Gly His Asn
            340                 345                 350

Phe Gly Met Asn His Asp Thr Leu Asp Arg Gly Cys Ser Cys Gln Met
        355                 360                 365

Ala Val Glu Lys Gly Gly Cys Ile Met Asn Ala Ser Thr Gly Tyr Pro
    370                 375                 380

Phe Pro Met Val Phe Ser Ser Cys Ser Arg Lys Asp Leu Glu Thr Ser
385                 390                 395                 400

Leu Glu Lys Gly Met Gly Val Cys Leu Phe Asn Leu Pro Glu Val Arg
                405                 410                 415

Glu Ser Phe Gly Gly Gln Lys Cys Gly Asn Arg Phe Val Glu Glu Gly
            420                 425                 430
```

```
Glu Glu Cys Asp Cys Gly Glu Pro Glu Cys Met Asn Arg Cys Cys
        435                 440                 445

Asn Ala Thr Thr Cys Thr Leu Lys Pro Asp Ala Val Cys Ala His Gly
    450                 455                 460

Leu Cys Cys Glu Asp Cys Gln Leu Lys Pro Ala Gly Thr Ala Cys Arg
465                 470                 475                 480

Asp Ser Ser Asn Ser Cys Asp Leu Pro Glu Phe Cys Thr Gly Ala Ser
                485                 490                 495

Pro His Cys Pro Ala Asn Val Tyr Leu His Asp Gly His Ser Cys Gln
            500                 505                 510

Asp Val Asp Gly Tyr Cys Tyr Asn Gly Ile Cys Gln Thr His Glu Gln
        515                 520                 525

Gln Cys Val Thr Leu Trp Gly Pro Gly Ala Lys Pro Ala Pro Gly Ile
    530                 535                 540

Cys Phe Glu Arg Val Asn Ser Ala Gly Asp Pro Tyr Gly Asn Cys Gly
545                 550                 555                 560

Lys Val Ser Lys Ser Ser Phe Ala Lys Cys Glu Met Arg Asp Ala Lys
                565                 570                 575

Cys Gly Lys Ile Gln Cys Gln Gly Gly Ala Ser Arg Pro Val Ile Gly
            580                 585                 590

Thr Asn Ala Val Ser Ile Glu Thr Asn Ile Pro Leu Gln Gln Gly Gly
        595                 600                 605

Arg Ile Leu Cys Arg Gly Thr His Val Tyr Leu Gly Asp Asp Met Pro
    610                 615                 620

Asp Pro Gly Leu Val Leu Ala Gly Thr Lys Cys Ala Asp Gly Lys Ile
625                 630                 635                 640

Cys Leu Asn Arg Gln Cys Gln Asn Ile Ser Val Phe Gly Val His Glu
                645                 650                 655

Cys Ala Met Gln Cys His Gly Arg Gly Val Cys Asn Asn Arg Lys Asn
            660                 665                 670

Cys His Cys Glu Ala His Trp Ala Pro Pro Phe Cys Asp Lys Phe Gly
        675                 680                 685

Phe Gly Gly Ser Thr Asp Ser Gly Pro Ile Arg Gln Ala Glu Ala Arg
    690                 695                 700

Gln Glu Ala Ala Glu Ser Asn Arg Glu Arg Gly Gln Gly Gln Glu Pro
705                 710                 715                 720

Val Gly Ser Gln Glu His Ala Ser Thr Ala Ser Leu Thr Leu Ile
                725                 730                 735

<210> SEQ ID NO 3
<211> LENGTH: 627
<212> TYPE: DNA
<213> ORGANISM: Homo sapiens

<400> SEQUENCE: 3
atgaagctgc tgccgtcggt ggtgctgaag ctctttctgg ctgcagttct ctcggcactg      60
gtgactggcg agagcctgga gcggcttcgg agagggctag ctgctggaac agcaacccg     120 gaccctccca ctgtatccac ggaccagctg ctaccctag gaggcggccg ggaccggaaa     180
gtccgtgact tgcaagaggc agatctggac cttttgagag tcactttatc ctccaagcca     240
caagcactgg ccacaccaaa caaggaggag cacgggaaaa gaagaagaa aggcaagggg      300 ctagggaaga agagggaccc atgtcttcgg aaatacaagg acttctgcat ccatggagaa     360
tgcaaatatg tgaaggagct ccgggctccc tcctgcatct gccacccggg ttaccatgga     420
```

-continued

| | |
|---|---|
| gagaggtgtc atgggctgag cctcccagtg gaaaatcgct tatataccta tgaccacaca | 480 |
| accatcctgg ccgtggtggc tgtggtgctg tcatctgtct gtctgctggt catcgtgggg | 540 |
| cttctcatgt ttaggtacca taggagagga ggttatgatg tggaaaatga agagaaagtg | 600 |
| aagttgggca tgactaattc ccactga | 627 |

<210> SEQ ID NO 4
<211> LENGTH: 2208
<212> TYPE: DNA
<213> ORGANISM: Homo sapiens

<400> SEQUENCE: 4

| | |
|---|---|
| atggcagcgc gcccgctgcc cgtgtccccc gcccgcgccc tcctgctcgc cctggccggt | 60 |
| gctctgctcg cgccctgcga ggcccgaggg gtgagcttat ggaaccaagg aagagctgat | 120 |
| gaagttgtca gtgcctctgt tgggagtggg gacctctgga tcccagtgaa gagcttcgac | 180 |
| tccaagaatc atccagaagt gctgaatatt cgactacaac gggaaagcaa agaactgatc | 240 |
| ataaatctgg aaagaaatga aggtctcatt gccagcagtt tcacggaaac ccactatctg | 300 |
| caagacggta ctgatgtctc cctcgctcga aattacacgg tcactgttac taccatggac | 360 |
| catgtacggg atattctgat tcagcagtca gtctcagca cgtgttctgg tctcagggga | 420 |
| cttattgtgt ttgaaaatga agctatgtc ttagaaccaa tgaaaagtgc aaccaacaga | 480 |
| tacaaactct cccagcgaa gaagctgaaa agcgtccggg atcatgtgg atcacatcac | 540 |
| aacacaccaa acctcgctgc aaagaatgtg tttccaccac cctctcagac atgggcaaga | 600 |
| aggcataaaa gagagaccct caaggcaact aagtatgtgg agctggtgat cgtggcagac | 660 |
| aaccgagagt ttcagaggca aggaaaagat ctggaaaaag ttaagcagcg attaatagag | 720 |
| attgctaatc acgttgacaa gttttacaga ccactgaaca ttcggatcgt gttggtaggc | 780 |
| gtggaagtgt ggaatgacat ggacaaatgc tctgtaagtc aggacccatt caccagcctc | 840 |
| catgaatttc tggactggag gaagatgaag cttctacctc gcaaatccca tgacaatgcg | 900 |
| cagcttgtca gtgggtttta tttccaaggg accaccatcg gcatggcccc aatcatgagc | 960 |
| atgtgcacgg cagaccagtc tgggggaatt gtcatggacc attcagacaa tcccettggt | 1020 |
| gcagccgtga ccctggcaca tgagctgggc cacaatttcg ggatgaatca tgacacactg | 1080 |
| gacaggggct gtagctgtca atggcggtt gagaaaggag gctgcatcat gaacgcttcc | 1140 |
| accgggtacc catttcccat ggtgttcagc agttgcagca ggaaggactt ggagaccagc | 1200 |
| ctggagaaag gaatggggt gtgcctgttt aacctgccgg aagtcaggga gtctttcggg | 1260 |
| ggccagaagt gtgggaacag atttgtggaa gaggagagg agtgtgactg tgggagcca | 1320 |
| gaggaatgta tgaatcgctg ctgcaatgcc accacctgta ccctgaagcc ggacgctgtg | 1380 |
| tgcgcacatg gctgtgctg tgaagactgc cagctgaagc ctgcaggaac agcgtgcagg | 1440 |
| gactccagca actcctgtga cctcccagag ttctgcacag ggccagccc tcactgccca | 1500 |
| gccaacgtgt acctgcacga tgggcactca tgtcaggatg tggacggcta ctgctacaat | 1560 |
| ggcatctgcc agactcacga gcagcagtgt gtcacgctct ggggaccagg tgctaaacct | 1620 |
| gcccctggga tctgctttga gagagtcaat tctgcaggtg atccttatgg caactgtggc | 1680 |
| aaagtctcga gagttccttt gccaaatgcg agatgagag atgctaaatg tggaaaaatc | 1740 |
| cagtgtcaag gaggtgccag ccggccagtc attggtacca atgccgtttc catagaaaca | 1800 |
| aacatccccc tgcagcaagg aggccggatt ctgtgccggg ggacccacgt gtacttgggc | 1860 |
| gatgacatgc cggacccagg gcttgtgctt gcaggcacaa agtgtgcaga tggaaaaatc | 1920 |

```
tgcctgaatc gtcaatgtca aaatattagt gtctttgggg ttcacgagtg tgcaatgcag    1980
tgccacggca gagggtgtg caacaacagg aagaactgcc actgcgaggc ccactgggca     2040
cctcccttct gtgacaagtt tggctttgga ggaagcacag acagcggccc catccggcaa    2100
gcagaagcaa ggcaggaagc tgcagagtcc aacaggagc gcggccaggg ccaggagccc     2160
gtgggatcgc aggagcatgc gtctactgcc tcactgacac tcatctga                 2208

<210> SEQ ID NO 5
<211> LENGTH: 24
<212> TYPE: DNA
<213> ORGANISM: Artificial Sequence
<220> FEATURE:
<223> OTHER INFORMATION: HB-EGF primer

<400> SEQUENCE: 5
acgtcgcgga tatcatgaag ctgc                                           24

<210> SEQ ID NO 6
<211> LENGTH: 22
<212> TYPE: DNA
<213> ORGANISM: Artificial Sequence
<220> FEATURE:
<223> OTHER INFORMATION: HB-EGF primer

<400> SEQUENCE: 6
acgtggcaga attctcagtg gg                                             22

<210> SEQ ID NO 7
<211> LENGTH: 20
<212> TYPE: DNA
<213> ORGANISM: Artificial Sequence
<220> FEATURE:
<223> OTHER INFORMATION: ADAM 12S primer

<400> SEQUENCE: 7
actgaaggcc ggcgatggca                                                20

<210> SEQ ID NO 8
<211> LENGTH: 27
<212> TYPE: DNA
<213> ORGANISM: Artificial Sequence
<220> FEATURE:
<223> OTHER INFORMATION: ADAM 12S primer

<400> SEQUENCE: 8
gtgaagcaag cttcagatga gtgtcag                                        27

<210> SEQ ID NO 9
<211> LENGTH: 21
<212> TYPE: DNA
<213> ORGANISM: Artificial Sequence
<220> FEATURE:
<223> OTHER INFORMATION: HB-EGF deltaN primer

<400> SEQUENCE: 9
atgcgggctc cctcctgcat c                                              21

<210> SEQ ID NO 10
<211> LENGTH: 22
<212> TYPE: DNA
<213> ORGANISM: Artificial Sequence
<220> FEATURE:
<223> OTHER INFORMATION: HB-EGF deltaN primer

<400> SEQUENCE: 10
```

-continued caacccgtac tgattaaggg tg                                                   22

<210> SEQ ID NO 11
<211> LENGTH: 24
<212> TYPE: DNA
<213> ORGANISM: Artificial Sequence
<220> FEATURE:
<223> OTHER INFORMATION: HB-EGF deltaC primer

<400> SEQUENCE: 11
acgtcgcgga tatcatgaag ctgc                                                 24

<210> SEQ ID NO 12
<211> LENGTH: 21
<212> TYPE: DNA
<213> ORGANISM: Artificial Sequence
<220> FEATURE:
<223> OTHER INFORMATION: HB-EGF deltaC primer

<400> SEQUENCE: 12
cctctccttt agtacctaaa c                                                    21

<210> SEQ ID NO 13
<211> LENGTH: 17
<212> TYPE: DNA
<213> ORGANISM: Artificial Sequence
<220> FEATURE:
<223> OTHER INFORMATION: PRDM16 primer

<400> SEQUENCE: 13
gaatggacaa acggcct                                                         17

<210> SEQ ID NO 14
<211> LENGTH: 19
<212> TYPE: DNA
<213> ORGANISM: Artificial Sequence
<220> FEATURE:
<223> OTHER INFORMATION: PRDM16 primer

<400> SEQUENCE: 14
tctacgtcct ctggctttg                                                       19

<210> SEQ ID NO 15
<211> LENGTH: 18
<212> TYPE: DNA
<213> ORGANISM: Artificial Sequence
<220> FEATURE:
<223> OTHER INFORMATION: PGC-1 alpha

<400> SEQUENCE: 15
accccagagt caccaaat                                                        18

<210> SEQ ID NO 16
<211> LENGTH: 19
<212> TYPE: DNA
<213> ORGANISM: Artificial Sequence
<220> FEATURE:
<223> OTHER INFORMATION: PGC-1 alpha primer

<400> SEQUENCE: 16
cacacttaag gttcgctca                                                       19

<210> SEQ ID NO 17
<211> LENGTH: 20
<212> TYPE: DNA
<213> ORGANISM: Artificial Sequence
<220> FEATURE:

```
<223> OTHER INFORMATION: UCP-1 primer

<400> SEQUENCE: 17
tcttcaggga gagaaacacc                                                 20

<210> SEQ ID NO 18
<211> LENGTH: 18
<212> TYPE: DNA
<213> ORGANISM: Artificial Sequence
<220> FEATURE:
<223> OTHER INFORMATION: UCP-1 primer

<400> SEQUENCE: 18
aatgaacact gccacacc                                                   18

<210> SEQ ID NO 19
<211> LENGTH: 20
<212> TYPE: DNA
<213> ORGANISM: Artificial Sequence
<220> FEATURE:
<223> OTHER INFORMATION: PPAR-gamma primer

<400> SEQUENCE: 19
ccacagttga tttctccagc                                                 20

<210> SEQ ID NO 20
<211> LENGTH: 20
<212> TYPE: DNA
<213> ORGANISM: Artificial Sequence
<220> FEATURE:
<223> OTHER INFORMATION: PPAR-gamma primer

<400> SEQUENCE: 20
gcaggttcta ctttgatcgc                                                 20

<210> SEQ ID NO 21
<211> LENGTH: 18
<212> TYPE: DNA
<213> ORGANISM: Artificial Sequence
<220> FEATURE:
<223> OTHER INFORMATION: C/EBP primer

<400> SEQUENCE: 21
ggacaagaac agcaacga                                                   18

<210> SEQ ID NO 22
<211> LENGTH: 18
<212> TYPE: DNA
<213> ORGANISM: Artificial Sequence
<220> FEATURE:
<223> OTHER INFORMATION: C/EBP primer

<400> SEQUENCE: 22
tcaactccag caccttct                                                   18

<210> SEQ ID NO 23
<211> LENGTH: 18
<212> TYPE: DNA
<213> ORGANISM: Artificial Sequence
<220> FEATURE:
<223> OTHER INFORMATION: AKT-1 primer

<400> SEQUENCE: 23
tcctcaagaa cgatggca                                                   18

<210> SEQ ID NO 24
```

```
<211> LENGTH: 18
<212> TYPE: DNA
<213> ORGANISM: Artificial Sequence
<220> FEATURE:
<223> OTHER INFORMATION: AKT-1 primer

<400> SEQUENCE: 24
actctcgctg atccacat                                                18

<210> SEQ ID NO 25
<211> LENGTH: 18
<212> TYPE: DNA
<213> ORGANISM: Artificial Sequence
<220> FEATURE:
<223> OTHER INFORMATION: GAPDH primer

<400> SEQUENCE: 25
ttgtggaagg gctcatga                                                18

<210> SEQ ID NO 26
<211> LENGTH: 17
<212> TYPE: DNA
<213> ORGANISM: Artificial Sequence
<220> FEATURE:
<223> OTHER INFORMATION: GAPDH primer

<400> SEQUENCE: 26
catcacgcca cagcttt                                                 17
```

CELL TRANSDIFFERENTIATION INTO BROWN ADIPOCYTES

CROSS-REFERENCE TO RELATED APPLICATIONS

This application claims priority to U.S. Provisional Patent Application Ser. No. 61/237,787, filed Aug. 28, 2009, which is incorporated herein by reference

GOVERNMENT FUNDING

The present invention was made with government support by the NIH-NIDCR under Grant No. 2R01DE 13570. The Government may have certain rights in this invention.

BACKGROUND

Obesity is a medical problem of increasing concern. An individual is defined as being clinically obese if they have a body mass index greater than 30 kg/m². In 1962, research statistics showed that the percentage of obesity in America's population was at 13%. By 1980 it has risen to 15%, by 1994 to 23%, and by the year 2000 the number of individuals in America categorized as being clinically obese had reached an unprecedented 31%. As a result, the health care service reports high morbidity and mortality from weight-related conditions such as cardiovascular disease and certain forms of cancer, and has seen a dramatic increase in type 2 diabetes mellitus. The U.S. Surgeon General report declared that obesity is responsible for 300,000 deaths every year. Understanding the molecular mechanisms underlying obesity has therefore become the object of an intense research effort.

Adipocytes typically develop from mesodermal stem cells, which can also differentiate into other mesenchymal cells such as muscle cells and osteoblasts. It has been shown that insulin, insulin-like growth factors, growth hormone, glucocorticoids, and catecholamines affect fat cell proliferation and differentiation in vivo and in vitro. See, for example, Gregoire et al., Physiol. Rev. 78, p. 783-809 (1998). In addition, metalloproteases can also be involved in adipogenesis, where they play a significant role in extracellular matrix (ECM) remodeling. See, for example, Lilla et al., Am J Pathol. 160, p. 1551-4 (2002).

ADAM 12 is a member of the family of proteins known as ADAMs (a disintegrin and metalloprotease). The ADAMs constitute a large family of multidomain membrane-anchored proteins that have been implicated in a number of biological activities, including extracellular-matrix remodeling, myogenesis, and adipogenesis. ADAM 12 exists in two forms: a membrane-bound long form, ADAM 12L, and an alternatively spliced secreted short form, ADAM 12S, which includes a prodomain and metalloprotease, disintegrin, cysteine-rich, and epidermal growth factor (EGF)-like domains. At the COOH-terminus, ADAM 12L contains a transmembrane domain and a cytoplasmic tail, whereas ADAM 12S is not membrane-anchored and contains a unique stretch of 33 amino acids.

Previous research using ADAM 12S transgenic mice under the transcriptional regulation of a muscle creatine kinase (MCK) promoter exhibit adipogenesis among muscle fibers as evidenced by Oil Red O staining and PPARγ positive cells (Kawaguchi et al., Am. J. Path., 160, p. 1895-1903 (2002)). Results from these transgenic mice suggest that ADAM 12S stimulated the formation of white adipose tissue. The authors indicated that both the membrane anchored ADAM 12L and the secreted forms of ADAM 12 (ADAM 12S) could stimulate adipogenesis.

Heparin-binding EGF-like growth factor (HB-EGF) is a membrane bound protein that is proteolytically processed by the soluble form of ADAM 12. HB-EGF has been implicated in a wide variety of disorders, including tumor growth, heart disease, and obesity. ADAM 12S stimulates ectodomain shedding of pro-HB-EGF, releasing a mature, soluble ligand (sHB-EGF) and a carboxyl-terminal fragment (HB-EGF-C) consisting of the transmembrane and cytoplasmic domains. Higashiyama et al., Biochim Biophys Acta., 1751, p. 110-7 (2005).

Mature, soluble HB-EGF and HB-EGF C are both known to stimulate cellular proliferation. Zhou et al., Cell Prolif., 40, p. 213-30 (2007). It was therefore the expectation that cells expressing both HB-EGF and ADAM 12 would exhibit significant cell proliferation as a result of proHB-EGF being proteolytically cleaved by ADAM 12S to provide soluble HB-EGF and HB-EGF C.

SUMMARY OF THE INVENTION

The inventors have surprisingly discovered that cells transformed to express both HB-EGF and ADAM 12 do not exhibit significant cell proliferation, as expected, but rather are converted from their original cell type to brown adipose tissue cells.

Accordingly, in one aspect the present invention provides a method for converting animal cells into brown adipose tissue cells that includes transforming the animal cells using an expression vector that includes a nucleotide sequence encoding HB-EGF operatively linked to a promoter and a nucleotide sequence encoding ADAM 12 operatively linked to a promoter.

In another aspect, the present invention provides a method of treating a subject diagnosed with obesity by transforming a portion of the white adipose tissue cells of the subject by administering an expression vector that includes a nucleotide sequence encoding HB-EGF operatively linked to an adipose-tissue specific promoter and a nucleotide sequence encoding ADAM 12 operatively linked to an adipose-tissue specific promoter.

In a further aspect, the present invention provides a method of treating a subject diagnosed with cancer by transforming a portion of the Cancer cells of the subject by administering an expression vector that includes a nucleotide sequence encoding HB-EFG operatively linked to a tumor specific promoter and a nucleotide sequence encoding ADAM 12 operatively linked to a tumor specific promoter.

BRIEF DESCRIPTION OF THE FIGURES

FIG. 2A provides the amino acid sequence for human HB-EGF (SEQ ID NO: 1) while FIG. 2B provides the nucleotide sequence for human HB-EGF (SEQ ID NO: 3).

FIG. 3 provides the amino acid sequence for human ADAM 12S (SEQ ID NO: 2).

FIG. 4 provides the nucleotide sequence for human ADAM 12S (SEQ ID NO: 4)

FIG. 8 provides bar graphs showing the expression of C/EBP-α, AKT-1, and PPAR-γ in white adipose tissue, and the expression of PRDM16, PBG-1α, and UCP-1α in brown adipose tissue.

DETAILED DESCRIPTION OF THE INVENTION

Figure 1:
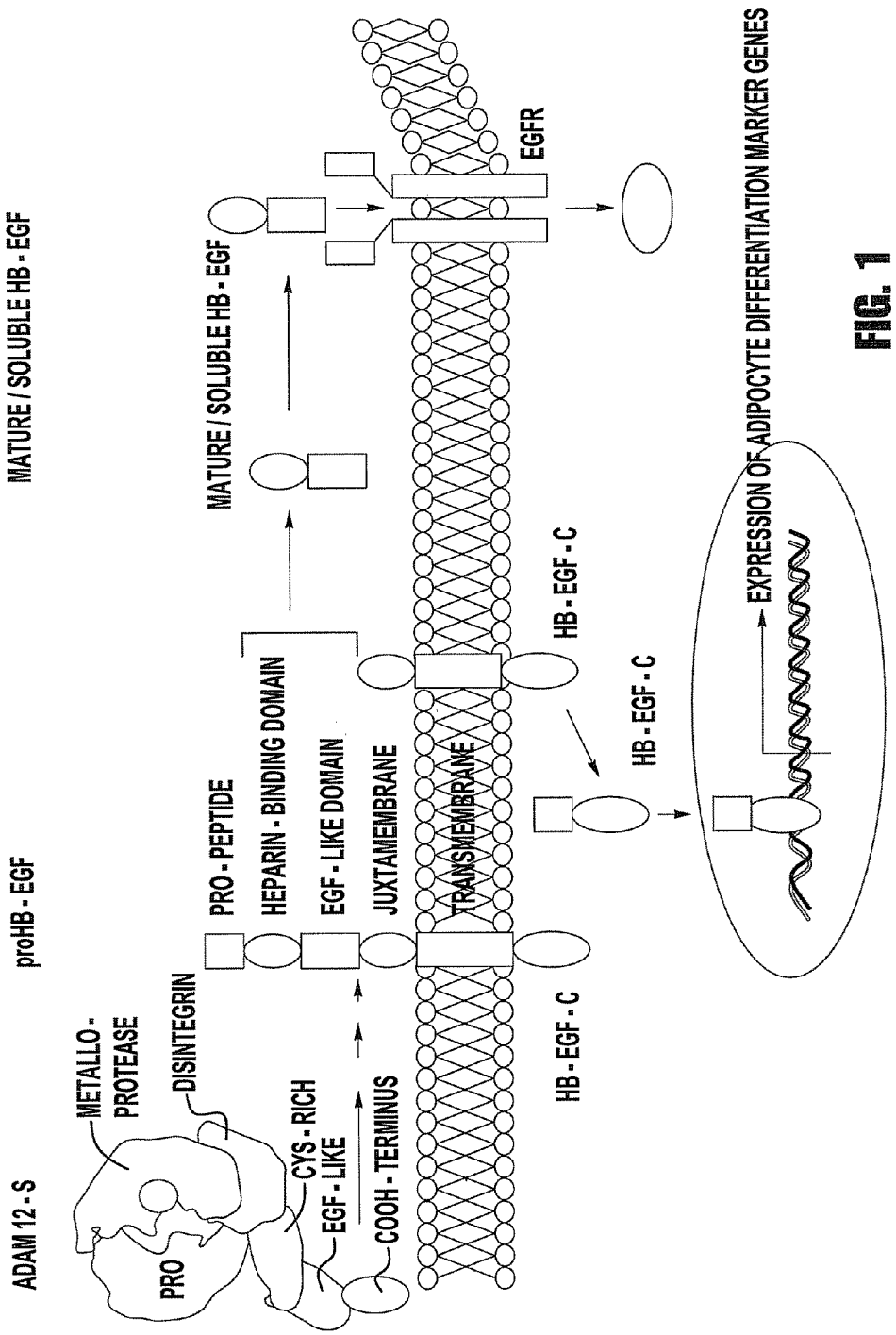
FIG. 1 provides a pictorial representation of the ectodomain shedding of HB-EGF.

The present invention provides a method for converting animal cells into brown adipose tissue cells by transforming the animal cells using an expression vector. The expression vector includes a nucleotide sequence encoding HB-EGF operatively linked to a promoter and a nucleotide sequence encoding ADAM 12 operatively linked to a promoter. Expression vectors of this type can be used to transdifferentiate various cell types, providing in some embodiments a gene therapy for obesity or for cancer.

Definitions

The terminology as set forth herein is for description of the embodiments only and should not be construed as limiting of the invention as a whole. Unless otherwise specified, "a," "an," "the," and "at least one" are used interchangeably. Furthermore, as used in the description of the invention and the appended claims, the singular forms "a", "an", and "the" are inclusive of their plural forms, unless contraindicated by the context surrounding such.

Also herein, the recitations of numerical ranges by endpoints include all numbers subsumed within that range (e.g., 1 to 5 includes 1, 1.5, 2, 2.75, 3, 3.80, 4, 5, etc.).

Adipose tissue as used herein refers to tissue composed primarily of adipocytes (i.e., fat cells), and functions primarily to store energy in the form of fat. Adipose tissue is characterized as either white adipose tissue (WAT) or brown adipose tissue (BAT).

White adipose tissue is composed primarily of white fat cells that contain a large lipid droplet surrounded by a layer of cytoplasm. The nucleus in white fat cells is flattened and located on the periphery. A typical white fat cell is about 0.1 mm in diameter, with some being twice that size and others half that size. The fat within a white fat cell is stored in a semi-liquid state, and is composed primarily of triglycerides and cholesteryl ester.

Brown adipose tissue is composed primarily of brown fat cells that are polygonal in shape. Unlike white fat cells, brown fat cells have considerable cytoplasm, with lipid droplets scattered throughout. The nucleus is round and is not located in the periphery of the cell. Brown fat cells also include a large quantity of mitochondria, which result in the brown color of the cells. Brown adipose tissue is also known as "baby fat" and is used physiologically to generate heat. Brown adipose tissue has a different embryological origin than white adipose tissue, and appears to share the same lineage as muscle. Enerbäck S, N Engl J Med 360, p. 2021-2023 (2009).

The term "polynucleotide" as used herein means a polymeric form of nucleotides of any length, either ribonucleotides or deoxyribonucleotides. This term refers only to the primary structure of the molecule. Thus, the term includes double- and single-stranded DNA, as well as double- and single-stranded RNA. It also includes modifications, such as methylation or capping, and unmodified forms of the polynucleotide. The terms "polynucleotide," "oligomer," "oligonucleotide," and "oligo" are used interchangeably herein.

"Amino acid" is used herein to refer to a chemical compound with the general formula: NH2-CRH—COOH, where R, the side chain, is H or an organic group. Where R is organic, R can vary and is either polar or nonpolar (i.e., hydrophobic). The following abbreviations for particular amino acids are used throughout the application: A=Ala=Alanine, T=Thr=Threonine, V=Val=Valine, C=Cys=Cysteine, L=Leu=Leucine, Y=Tyr=Tyrosine, I=Ile=Isoleucine, N=Asn=Asparagine, P=Pro=Proline, Q=Gln=Glutamine, F=Phe=Phenylalanine, D=Asp=Aspartic Acid, W=Trp=Tryptophan, E=Glu=Glutamic Acid, M=Met=Methionine, K=Lys=Lysine, G=Gly=Glycine, R=Arg=Arginine, S=Ser=Serine, H=His=Histidine.

A nucleotide consists of a phosphate group linked by a phosphoester bond to a pentose (ribose in RNA, and deoxyribose in DNA) that is linked in turn to an organic base. The monomeric units of a nucleic acid are nucleotides. Naturally occurring DNA and RNA each contain four different nucleotides: nucleotides having adenine, guanine, cytosine and thymine bases are found in naturally occurring DNA, and nucleotides having adenine, guanine, cytosine and uracil bases found in naturally occurring RNA. The bases adenine, guanine, cytosine, thymine, and uracil often are abbreviated A, G, C, T and U, respectively.

Nucleotides include free mono-, di- and triphosphate forms (i.e., where the phosphate group has one, two or three phosphate moieties, respectively). Thus, nucleotides include ribonucleoside triphosphates (e.g., ATP, UTP, CTG and GTP) and deoxyribonucleoside triphosphates (e.g., dATP, dCTP, dITP, dGTP and dTTP), and derivatives thereof. Nucleotides also include dideoxyribonucleoside triphosphates (ddNTPs, including ddATP, ddCTP, ddGTP, ddITP and ddTTP), and derivatives thereof.

The phrases "percent identity" and "percent identical," in the context of two nucleic acid or protein sequences, refer to two or more sequences or subsequences that have in some embodiments a specified matching level when compared and aligned for maximum correspondence, as measured using one of the following sequence comparison algorithms or by visual inspection. The percent identity exists in some embodiments over a region of the sequences that is at least about 50 residues in length, in some embodiments over a region of at least about 100 residues, and in some embodiments the percent identity exists over at least about 150 residues. In some embodiments, the percent identity exists over the entire length of a given region, such as a coding region.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, for example, by the local homology algorithm described in Smith & Waterman, 1981, by the homology alignment algorithm described in Needleman & Wunsch, 1970, by the search for similarity method described in Pearson & Lipman, 1988, by computerized implementations of these algorithms (GAP, BESTFIT, FASTA, and TFASTA in the GCG® WISCONSIN PACKAGE® available from Accelrys, Inc., San Diego, Calif., United States of America), or by visual inspection. See generally, Ausubel et al., eds Current Protocols in Molecular Biology. Wiley, New York (1989).

One example of an algorithm that is suitable for determining percent sequence identity and sequence similarity is the BLAST algorithm, which is described in Altschul et al., J Mol Biol 215, 403-410 (1990). Software for performing BLAST analyses is publicly available through the National Center for Biotechnology Information via the World Wide Web. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., 1990). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix. See Henikoff & Henikoff, Proc Natl Acad Sci USA 89, 10915-10919 (1992).

"Substantially similar" means that a given nucleic acid or amino acid sequence shares at least 85%, more preferably at least 90%, and even more preferably at least 95% identity with a reference sequence. Furthermore, while it is possible to have nonconservative amino acid substitutions in substantially similar sequences, it is preferred that substitutions be conservative amino acid substitutions, in which the substituted amino acid has similar structural or chemical properties with the corresponding amino acid in the reference sequence. By way of example, conservative amino acid substitutions involve substitution of one aliphatic or hydrophobic amino acids, e.g., alanine, valine, leucine and isoleucine, with another; substitution of one hydroxyl-containing amino acid, e.g., serine and threonine, with another; substitution of one acidic residue, e.g., glutamic acid or aspartic acid, with another; replacement of one amide-containing residue, e.g., asparagine and glutamine, with another; replacement of one aromatic residue, e.g., phenylalanine and tyrosine, with another; replacement of one basic residue, e.g., lysine, arginine and histidine, with another; and replacement of one small amino acid, e.g., alanine, serine, threonine, methionine, and glycine, with another.

The term "isolated" means that the material is removed from its original environment (e.g., the natural environment if it is naturally occurring). For example, a naturally occurring polynucleotide or polypeptide present in a living animal is not isolated, but the same polynucleotide or DNA or polypeptide that is separated from some or all of the coexisting materials in the natural system, is isolated. Such polynucleotide could be part of a vector or such polynucleotide or polypeptide could be part of a composition, and still be isolated in that the vector or composition is not part of its natural environment.

The term "vector" refers to a nucleic acid capable of transporting another nucleic acid to which it has been linked. One type of vector that can be used in accord with the presently disclosed subject matter is a retroviral vector, i.e., a nucleic acid capable of integrating the nucleic acid sequence of interest into the host cell chromosome. Other vectors include those capable of autonomous replication and expression of nucleic acids to which they are linked. Vectors capable of directing the expression of genes to which they are operatively linked are referred to herein as "expression vectors". In general, expression vectors of utility in recombinant DNA techniques are often in the form of plasmids. However, the presently disclosed subject matter is intended to include such other forms of expression vectors which serve equivalent functions (e.g., retroviral vectors such as adenoviral vectors, cosmids or bacmids) or and which become known in the art subsequently hereto.

The term "expression vector" as used herein refers to a DNA sequence capable of directing expression of a particular nucleotide sequence in an appropriate host cell. Expression vectors can contain a variety of control sequences (e.g., promoters and terminators), structural genes (e.g., genes of interest), and nucleic acid sequences that serve other functions as well. The construct comprising the nucleotide sequence of interest can be chimeric. The nucleotide sequence of interest, including any additional sequences designed to effect proper expression of the nucleotide sequences, can also be referred to as an "expression cassette".

The term "transfection" refers to the introduction of a nucleic acid, e.g., an expression vector, into a recipient cell, which in certain instances involves nucleic acid-mediated gene transfer. The term "transformation" refers to a process in which a cell's genotype is changed as a result of the cellular uptake of heterologous nucleic acid. For example, a transformed cell can express a protein such as HB-EGF or ADAM 12 that is not present in the typical genotype of the cell.

The transformation of a cell with a heterologous nucleic acid (for example, an expression vector) can be characterized as transient or stable. As used herein, the term "stable" refers to a state of persistence that is of a longer duration than that which would be understood in the art as "transient". These terms can be used both in the context of the transformation of cells (for example, a stable transformation), or for the expression of a transgene (for example, the stable expression of a gene encoding a sugar metabolizing enzyme) in a transgenic cell. In some embodiments, a stable transformation results in the incorporation of the heterologous nucleic acid molecule (for example, an expression vector) into the genome of the transformed cell. As a result, when the cell divides, the vector DNA is replicated along with plant genome so that progeny cells also contain the heterologous DNA in their genomes. Transformation of plastid or other self replicating organelle based nucleic acids (e.g., mitochondrial DNA) is also contemplated under this definition.

An animal cell as used herein refers to a eukaryotic cell of an animal, preferably a mammal. Animal cells may exist in an animal or in cell culture. A subject as used herein is preferably a mammal, such as a domesticated farm animal (e.g., cow, horse, a pig) or pet (e.g., dog, cat). More preferably, the subject is a human.

A cancer cell as defined herein is an animal cell including genetic abnormalities that result in the relatively uncontrolled proliferation of the cell, leading to tumor formation and the disease cancer. The genetic abnormalities found in cancer cells are typically either activation of cancer-promoting oncogenes or inactivation of tumor suppressor genes. Activation of cancer-promoting oncogenes gives the cells new properties, such as hyperactive growth and division, protection against programmed cell death, loss of respect for normal tissue boundaries, and the ability to become established in diverse tissue environments. Inactivation of tumor suppressor genes results in the loss of normal functions in those cells, such as accurate DNA replication, control over the cell cycle, orientation and adhesion within tissues, and interaction with protective cells of the immune system. A tumor refers to a significant mass of cancer cells.

Transdifferentiation as used herein describes the conversion of a non-stem cell into a different type of cell. Transdifferentiation is a type of metaplasia, which is the replacement of one differentiated cell type with another differentiated cell type. It is generally caused by some sort of abnormal stimulus such as a dramatic change in the cell's environment. Cell types are distinct morphological or functional forms of cells.

Operatively linked as used herein refers to bringing a polynucleotide coding sequence under the control of a promoter. "Operatively linking" a sequence to a promoter means one positions the 5' end of the transcription initiation site of the transcriptional reading frame of the protein between about 1 and about 50 nucleotides "downstream" of (i.e., 3' of) the chosen promoter. In addition, where eukaryotic expression is contemplated, one will also typically desire to incorporate into the transcriptional unit (which includes the cotransporter protein) an appropriate polyadenylation site if one was not contained within the original cloned segment. Typically, the poly A addition site is placed about 30 to 2000 nucleotides "downstream" of the termination site of the protein at a position prior to transcription termination. Appropriate spacing of promoters and the polynucleotide sequences whose expression they govern is well known by those skilled in the art.

The polynucleotide encoding a gene product is under the transcriptional control of a promoter. A "promoter" as used herein refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation and expression of the gene.

A promoter is typically a group of transcriptional control modules that are clustered around the initiation site for RNA polymerase II. Recent work has shown that promoters are typically composed of discrete functional modules, each consisting of approximately 7-20 bp of DNA, and containing one or more recognition sites for transcriptional activator or repressor proteins. At least one module in each promoter functions to position the start site for RNA synthesis. The best known example of this is the TATA box. Additional promoter elements may regulate the frequency of transcriptional initiation.

Termination of transcription of a polynucleotide sequence is typically regulated by an operatively linked transcription termination sequence (for example, an RNA polymerase termination sequence). In certain instances, transcriptional terminators are also responsible for correct mRNA polyadenylation. The 3' non-transcribed regulatory DNA sequence includes from in some embodiments about 50 to about 1,000, and in some embodiments about 100 to about 1,000, nucleotide base pairs and contains transcriptional and translational termination sequences. Appropriate transcriptional terminators for use in animal subjects are known to those skilled in the art.

In one aspect, the present invention provides a method for converting animal cells into brown adipose tissue cells. This method includes transforming the animal cells using an expression vector to include a polynucleotide sequence encoding HB-EGF operatively linked to a promoter and a polynucleotide sequence encoding ADAM 12 operatively linked to a promoter.

Accordingly, the inventors have found that animals cells can be converted or "transdifferentiated" from their initial cell type to brown adipose tissue cells if the cells are transformed to express both HB-EGF and ADAM 12. While not intending to be bound by theory, the inventors believe that ADAM 12 proteolytically cleaves membrane-bound proHB-EGF, resulting in the release of soluble HB-EGF outside the cell (i.e., ectodomain shedding) which interacts with EGF receptors, and the release of HB-EGF-C within the cell, which then migrates to the cell nucleus (i.e., translocates) where it stimulates the expression of various adipocyte differentiation marker genes. The ectodomain shedding of HB-EGF is shown in FIG. 1.

A variety of different types of cells can be caused to transdifferentiate into brown adipose cells as a result of transfection with an expression vector including the polynucleotide sequences for ADAM 12 and HB-EGF. The transdifferentiated cells can be animal cells or mammal cells. If mammalian cells are used, the cells can be obtained, for example, from a human or from mammalian pets such as dogs or cats or from domesticated mammals such as pigs, cows, and horses.

In further embodiments of the invention, the animal cell can be any known cell type. For example, human beings have about 210 different cell types, found in various different systems within the body. For example, cells from the cartilage/bone/muscle/integumentary system include cell types such as osteoblasts, osteocytes, osteoclasts, cementoblasts, ameloblasts, chondroblasts, chondrocytes, trichocytes, keratinocytes, melanocytes, myocytes, adipocytes, fibroblasts, and tendon cells, all of which may provide target cells for transdifferentiation into adipocytes. The different cell types are known to those skilled in the art. Examples of cell types that are preferred targets of the present invention are white adipose tissue cells, cancer cells, and fibrobast cells.

Transdifferentiation of cells in a tissue may result in varying percentages of conversion to brown adipose tissue cells. The number of cells converted depends on a variety of factors, with the transduction efficiency being a major factor. In some embodiments, up to 100% of the cells in a target tissue can be converted, whereas in other embodiments up to 90%, 80%, 70%, 60%, 50%. 40%, 30%, 20%, 10%, or 5% of the animal cells are converted to brown adipose tissue cells. These brown adipose tissue cells will have high levels of mitochondria, and exhibit high levels of thermogenesis. In addition, the brown adipose cells will typically also be non-proliferating cells, even in situations such as the conversion of cancer cells where the cells originally had a higher rate of proliferation.

ADAM 12 exists in two forms; ADAM 12S, which is the shorter, secreted form, and ADAM 12L, which is a membrane-anchored form of the protein. Both forms of ADAM 12 include a proteolytic site capable of cleaving HB-EGF. Accordingly, both forms of ADAM 12 are suitable for use in the invention for expression together with HB-EGF to transdifferentiate cells into brown adipocytes. Therefore, ADAM 12 as used herein refers to both the 12L and the 12S forms of ADAM 12. Furthermore, while portions of the application focus on the use and expression of ADAM 12S, it should be appreciated that ADAM 12L can also be used in the manner described for ADAM 12S.

The polypeptides that result in the transdifferentiation of target cells are the metalloprotease ADAM 12 and the growth factor HB-EGF. The polypeptide sequence of human HB-EGF is provided by SEQ ID NO: 1, shown in FIG. 2A. The polypeptide sequence of human ADAM 12S is provided by SEQ ID NO: 2, shown in FIG. 3. These polypeptides, as well as polypeptides that are substantially similar such as active fragments or variants thereof, will stimulate transdifferentiation of cells to brown adipocytes when they are co-expressed in animal cells. Nucleotide sequences encoding human ADAM 12S (SEQ ID NO: 3) and human HB-EGF (SEQ ID NO: 4) are also provided in FIGS. 2B and 4, respectively.

The present invention provides a method of transforming animal cells using an expression vector that includes a nucleotide sequence encoding HB-EGF operatively linked to a promoter and a nucleotide sequence encoding ADAM 12 operatively linked to a promoter. Both the HB-EGF and the ADAM 12 that are encoded by these nucleotide sequences include sequences that express proteins that are substantially similar to SEQ ID NO: 1 and SEQ ID NO: 2, respectively, as defined herein, and retain a substantial portion of the activity of the native proteins. In some embodiments, the expression vector that encodes the HB-EGF and the ADAM 12 can be a single expression vector. In other embodiments, separate expression vectors can be used to provide HB-EGF and ADAM 12. The nucleotide sequences used to encode HB-EGF and ADAM 12 can also vary substantially as a result of the redundancy present in tRNA, which various nucleotide triplets in the anticodon can be used to encode the same amino acid during translation. Other control elements for expression of the HB-EGF and ADAM-12, such as transcription factor binding sites and termination sequences, can also be included in the expression vector.

The inventor has cloned and sequenced human HB-EGF and ADAM 12S, and by sequence comparison in Genbank has identified several homologs. These amino acid sequences for HB-EGF and ADAM 12S from mouse, human, rat, canine, monkey, hamster, chicken, and bovine share from 72 to 93 percent identity to HB-EGF and 88 to 98 percent identity to ADAM 12S, respectively. It is well known that amino acid sequences, which are highly conserved between species, are also likely to be functional across different species, whereas non-conserved amino acid sequences may often be substituted without a loss of activity or diverse activity. It is also known that polypeptide fragments with conserved amino acid sequences are likely to possess the various functional activities of the intact polypeptide.

One of ordinary skill in the art will appreciate that by encoding shorter polypeptide fragments of ADAM 12 and expressing them in a cell, one would be able to identify polypeptides of fewer residues that possess the HB-EGF-activating properties of the ADAM 12 polypeptide (e.g., ADAM 12S; SEQ ID NO: 2). Similarly, one of ordinary skill in the art will appreciate that encoding shorter peptide fragments of the HG-EGF polypeptide (SEQ ID NO: 1) and expressing them in a cell, one would be able to identify polypeptides of fewer resides that possess the ability to stimulate adipocyte transdifferentiation upon activation by ADAM 12. One of ordinary skill in the art will also appreciate that various mutations or derivations of this polypeptide sequence, including amino acid substitutions, insertions, or modifications, may also result in an ADAM 12 polypeptide with increased or decreased HB-EGF activating capacity that is nonetheless substantially similar to human ADAM 12. Likewise, various mutations or derivatives of the polypeptide sequence of HB-EGF will result in HB-EGF polypeptides that retain the ability to stimulate adipocyte transdifferentiation upon activation and are substantially similar to human HB-EGF.

The ability of modified ADAM 12 polypeptides to activate HB-EGF, or the ability of modified HB-EGF polypeptides to stimulate adipocyte transdifferentiation upon activation can be readily evaluated through screening to identify active modified forms. For example, since it is known that ADAM 12S is able to process proHB-EGF to produce both the amino-terminal soluble, mature HB-EGF and the carboxy-terminal HB-EGF C, incubation of ADAM 12S protein with membrane bound proHB-EGF (21 kDa and 24 kDa) will yield both soluble, mature HB-EGF (14 kDa) and HB-EGF C (6.5 kDa) proteins. Western blot analysis using antibodies to recognize amino-terminal HB-EGF or carboxy-terminal HB-EGF are available to detect the ADAM 12S processed proteins.

Polynucleotide sequences such as SEQ ID NO: 4 or substantially similar sequences encoding ADAM 12 (e.g., ADAM 12S) or active fragments thereof will express an ADAM 12 polypeptide protease when introduced into the nucleus of an animal cell. This protease will activate HB-EGF expressed by the same or nearby cells as a result of the incorporation and expression of HB-EGF, activating the EGF receptor and expression of adipocyte differentiation genes, resulting in the transdifferentiation of the animal cells into brown adipose tissue cells. HB-EGF is expressed as a result of the expression of polynucleotide sequences such as SEQ ID NO: 3 or substantially similar sequences.

A number of transfection techniques for introducing polynucleotide sequences into animal cells are well known in the art and are disclosed herein. See, for example, Graham et al., Virology, 52: 456 (1973); Sambrook et al., Molecular Cloning, A laboratory Manual, Cold Spring Harbor Laboratories (New York, 1989); Davis et al., Basic Methods in Molecular Biology, Elsevier, 1986; and Chu et al., Gene, 13: 197 (1981). Such techniques can be used to introduce one or more exogenous polynucleotide sequences and their associated promoters into animal cells.

Figure 5:
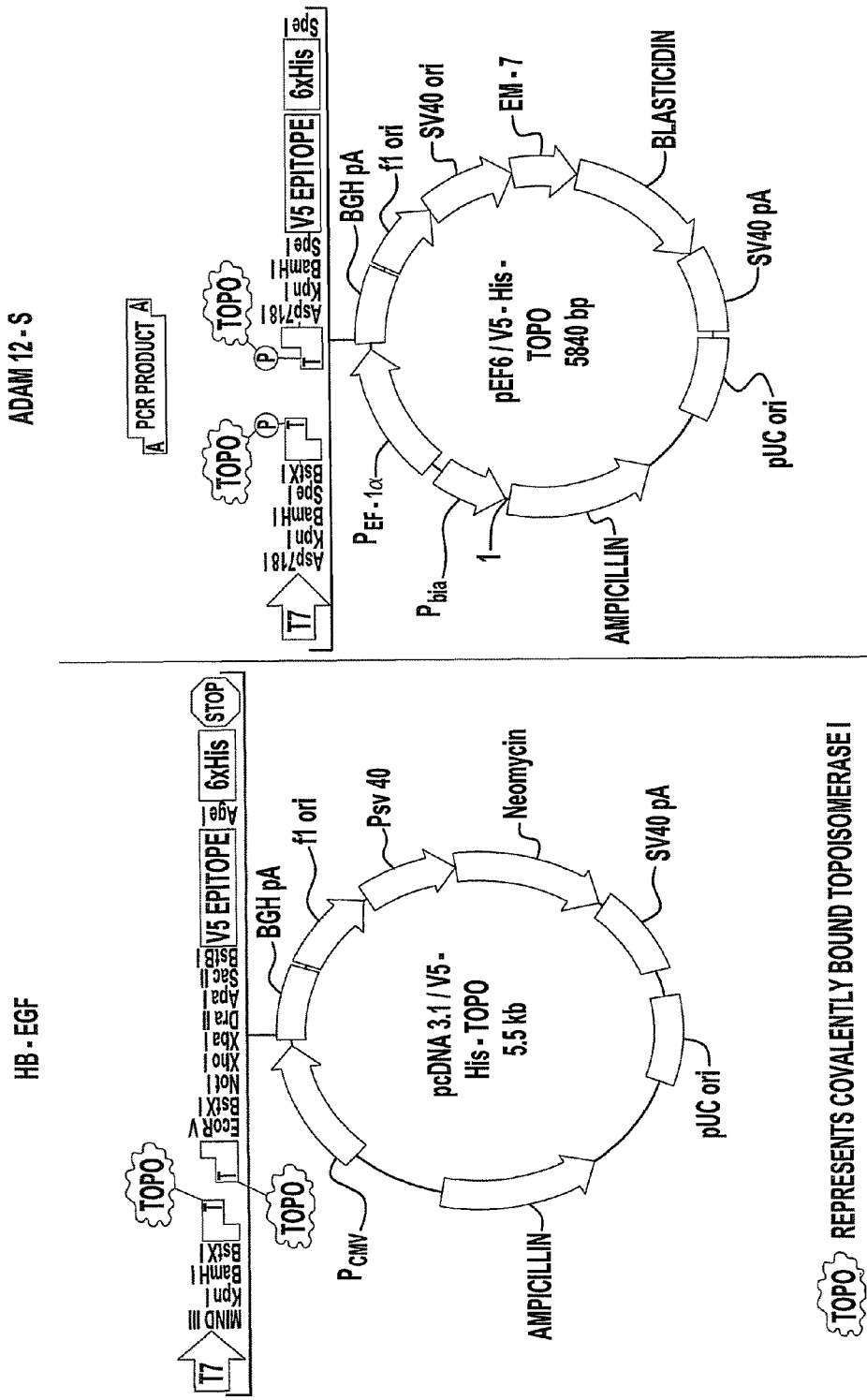
FIG. 5 shows the vectors pcDNA3.1/V5-His-TOPO (in WA) and pEF6/V5-His-TOPA (in WB) which were used to transform cells with HB-EGF or ADAM 12S, respectively.

The expression vector carrying the polynucleotide sequences encoding HB-EGF and ADAM 12 can be any type of expression vector suitable for the delivery of polynucleotide sequences to animal cells. A broad variety of suitable expression vectors are available for introducing polynucleotide sequences into animal cells, including plasmids, cosmids, yeast artificial chromosomes, and viral vectors. Viral vectors include retroviral-based vectors such as lentivirus, adenovirus vectors, AAV vectors, SV40 virus vectors, herpes simplex viral vectors, human cytomegalovirus vectors, Epstein-Barr virus vectors, poxvirus vectors, negative-strand RNA viral vectors such as influenza virus vectors, alpha virus vectors, and herpesvirus saimiri virus vectors, all of which have been demonstrated to be suitable for gene transfection. Examples of plasmid vectors suitable for use include the pcDNA3.1/V5-His-TOPO and pEF6/V5-His TOPO expression vectors, shown in FIG. 5. A particularly preferred viral vector is the adenovirus vector, which has the advantage of resulting in a high levels of gene expression and being able to insert relatively large polynucleotide sequences.

Viral vectors may be used to deliver one or more polynucleotide sequences to adipocytes in some embodiments. Delivery to adipocytes under in vitro and in vivo conditions is described by Casteilla et al., Current Gene Therapy, 8, p. 79-87 (2008), the disclosure of which is incorporated herein by reference. Preferred viral vectors for delivery to adipocytes include lentivirus and adenovirus.

In some embodiments of the invention, the expression vectors are introduced directly to a subject in vivo. Various expression vectors are particularly suitable for in vivo gene therapy applications. For example, viral vectors and non-viral vectors such as cationic liposomes, calcium phosphate precipitates, and receptor-mediated poly-lysine-DNA complexes are suitable for use in gene therapy. See, for example, Claudio et al., Clin. Canc. Res. 6, p. 754-764 (2000) which describes the use of various vectors in the gene therapy of lung cancer.

The expression vector preferably also includes a promoter that is operatively linked to the polynucleotide sequence being expressed. The particular promoter that is employed to control the expression of a nucleic acid encoding a particular gene is not believed to be important, so long as it is capable of expressing the nucleic acid in the targeted cell. Thus, where a human cell is targeted, it is preferable to position the nucleic acid coding region adjacent to and under the control of a promoter that is capable of being expressed in a human cell.

In various instances, the human cytomegalovirus (CMV) immediate early gene promoter, the SV40 early promoter and the Rous sarcoma virus long terminal repeat can be used to obtain high-level expression of the gene of interest. The use of other viral or mammalian cellular or bacterial phage promoters which are well-known in the art to achieve expression of a gene of interest is contemplated as well, provided that the levels of expression are sufficient for a given purpose.

In pCDA2 expression vector may be used in some embodiments of the invention. The cytomegalovirus promoter was used in this expression vector because it is able to drive expression in numerous cell types and tissues, and could be selected for using the G418 antibiotic (i.e., Genetecin). As another example, the elongation factor promoter (pEF6) was used to stimulate the expression of ADAM 12S because this vector had a different selection marker (blasticidin). Use of different selection markers in the expression vectors for HB-EGF and ADAM 12 is preferable because it allows one to select independently and together. For example, in different embodiments the inventors transfected normal mouse fibroblasts with proHB-EGF (G418 selection) or ADAM 12S (blasticidin selection) or HB-EGF and ADAM 12S (selected with both G418 and blasticidin). All non-transfected cells (i.e., cells that did not incorporate the plasmid) eventually die and are thus not selected. Selection of transfected cells is particularly useful when modifying cells ex vivo.

In some embodiments the HB-EGF and ADAM 12 expression vectors are targeted to cells of a particular tissue. This can be facilitated by delivery of the expression vectors at a particular tissue site, or using an expression vector that exhibits preferential transformation of the target cells. For example, adenovirus has been reported to preferentially transduce mature adipocytes. When targeting cells of a particular tissue, the HB-EGF and ADAM 12 are preferably introduced into the cells of the particular tissue under the control of a tissue specific promoter to allow targeted transdifferentiation of that particular tissue. This will result in the expression of HB-EGF and ADAM 12 at significant levels only in the targeted tissue.

For example, the HB-EGF and ADAM 12 expression vectors may be expressed in liver cells under the control of a liver specific promoter, such as the transthyretin (TTR), glucose 6 phosphatase, or albumin promoters. The HB-EGF and ADAM 12 expression vectors may be expressed in intestinal cells under the control of a promoter specific to intestinal cells, such as the intestinal fatty acid binding protein (IFABP) promoter. The HB-EGF and ADAM 12 expression vectors may be expressed in lung cells under the control of a promoter specific to lung cells, such as the surfactant A or surfactant C promoter. The HB-EGF and ADAM 12 expression vectors may be expressed in thyroid cells under the control of a promoter specific to thyroid cells such as the thyroglobulin promoter.

In some embodiments, the expression vectors may be expressed in adipose cells under the control of an adipose-tissue specific promoter. For example, the aP2 adipose specific enhancer is a promoter that has been used to achieve adipose-restricted expression, as described by Valet et al., J. Lipid Res. 43, 835-60 (2002). Use of the aP2 adipose specific enhancer has the further advantage of also being effective in macrophages found in adipose tissue, which appear to play a role in regulating the plasticity of adipose tissue. Another promoter suitable for restricting gene expression to adipose tissue is a leptin promoter. Expression of HB-EGF and ADAM 12 in white adipose tissue can provide a method of treating obesity by transdifferentiating white adipose cells, which specialize in energy storage, into brown adipose cells, which specialize in dissipating stored energy.

Transdifferentiation of target cells to brown adipose tissue cells can be used for various methods of treatment. Treatment as used herein refers to a method that decreases, or in some cases completely eliminates, the pathology of disease or disorder. For example, transdifferentiation of white adipose tissue cells to brown adipose tissue cells may be used as a treatment for obesity. Brown adipose tissue cells carry out thermogenesis rather than fat storage, resulting in an increase in the amount of calories expended by tissue. As obesity is the result of an excessive accumulation of calories, this can help reverse the accumulation of fat as a result of providing an increased overall metabolism. Furthermore, because adipose tissue cells are relatively stable and long-lived, transdifferentiation can provide significant benefits even if progeny cells revert back to their original type.

In other embodiments, the expression vectors may be expressed cancer cells under the control of a tumor-specific promoter. The tumor-specific promoter used should be one known to be significant in the cancer cell being targeted. A large variety of tumor specific promoters are known to those skilled in the art, and particular tumor-specific promoters are known to be involved in the pathogenesis of one or more cancer species. For example, cdc25a is a tumor-specific promoter that is upregulated in many different types of cancer. Accordingly, in some embodiments, the expression vector includes a tumor specific promoter operatively linked to at least one of the nucleotide sequence encoding HB-EGF and the nucleotide sequence encoding ADAM 12.

Cancer cells of various different types of cancer can be treated using promoters that result in the selective expression of HB-EGF and ADAM 12 in the targeted cells. Examples of types of cancer that can be treated by gene therapy with an expression vector resulting in HB-EGF and ADAM 12 expression include carcinomas, sarcomas, leukemias, and lymphomas. Carcinoma is cancer that begins in the skin or in tissues that line or cover internal organs, such as skin cancer. Sarcoma is cancer that begins in bone, cartilage, fat, muscle, blood vessels, or other connective or supportive tissue, such as lung cancer. Leukemia is cancer that starts in blood-forming tissue such as the bone marrow, and causes large numbers of abnormal blood cells to be produced and enter the bloodstream. Lymphoma and multiple myeloma are cancers that begin in the cells of the immune system. An example of a specific type of cancer that can be treated by the present method is retinoblastoma. When a tumor does not contain cysts or liquid areas, it is generally referred to as a solid tumor. Carcinomas, sarcomas, and lymphomas often form a solid tumor, whereas leukemias generally do not.

In some embodiments, transdifferentiation of cancer cells on the outside of a tumor mass can also result in transdifferentiation of cancer cells within the tumor mass as a result of exposure of these cancer cells to high levels of expressed HB-EGF and ADAM 12.

In certain embodiments, gene transfer may more easily be performed under ex vivo conditions. Ex vivo treatment refers to the isolation of cells from an animal, the delivery of a nucleic acid into the cells in vitro, and then the return of the modified cells back into an animal. This may involve the surgical removal of tissue/organs from an animal or the primary culture of cells and tissues. U.S. Pat. No. 5,399,346 by Anderson et al., which is incorporated herein by reference, discloses ex vivo therapeutic methods that can be readily applied to conversion of animal cells to adipocytes according to the present invention.

The present invention is illustrated by the following examples. It is to be understood that the particular examples, materials, amounts, and procedures are to be interpreted broadly in accordance with the scope and spirit of the invention as set forth herein.

EXAMPLES

Example 1

Cloning of Human HB-EGF and Human ADAM 12S Expression Vector

Both human HB-EGF cDNA (627 bp) and human ADAM 12S cDNA (2,217 bp) were amplified by PCR from the plasmid pIRES:EGFP/hHB-EGF and pcDNA 3.0, respectively. PCR reactions contained 4 ng/µl of HB-EGF cDNA or ADAM 12S cDNA, 0.5 µl forward and reverse primers (10 µM), 2.0 µl of 10× reaction buffer, 0.5 µl dNTPs, 0.5 µl Taq polymerase (New England Biolabs, Beverly, Mass.), and dH$_2$O to bring the volume to 20 µl. Each reaction was subjected to 94° C. (5 min), 35 cycles of 94° C. (30 s), 58° C. (1 min), and 72° C. (40 s), followed by an extension at 72° C. (10 min). Reaction products were separated by 0.8% agarose gel electrophoresis. The fragments of HB-EGF cDNA and ADAM 12S cDNA were then purified using gel extraction kit (QIAGEN), and cloned into pcDNA3.1/V5-His-TOPO and pEF6/V5-His TOPO expression vector, respectively (Invitrogen), shown in FIG. 5. The resulting plasmids were transformed into competent E. coli, isolated using QIAGEN Plasmid Midi Kit (QIAGEN), and sequenced using ABI 3730 Genetic Analyzer. The plasmids with correct orientation of HB-EGF cDNAs and ADAM 12S cDNAs were transfected into mouse fibroblasts and human epidermoid carcinoma cells. Following are primers for amplifying human HB-EGF and human ADAM 12S:

| Gene | Forward and Reverse primers | |
|---|---|---|
| HB-EGF | 5'-ACG TCG CGG ATA TCA TGA AGC TGC-3' | (SEQ ID NO: 5) |
| | 5'-ACG TGG CAG AAT TCT CAG TGG G-3' | (SEQ ID NO: 6) |
| ADAM 12S | 5'-ACT GAA GGC CGG CGA CGA TGG CA-3' | (SEQ ID NO: 7) |
| | 5'-GTG AAG CAA GCT TCA GAT GAG TGT CAG-3' | (SEQ ID NO: 8) |

Example 2

Construction of HB-EGF$_{\Delta N}$ and HB-EGF$_{\Delta C}$ Deletion Mutants

The full-length 627-bp human HB-EGF cDNA has previously been cloned into the MT-1 expression vector, pMT-1: HB-EGF (Harding et al. Growth Factors, 17, p. 49-61 (1999)). A 558 bp human HB-EGF cDNA encoding nucleotides 1-558 of exon 1 through exon 5 including a translational stop codon and a 246 bp human HB-EGF cDNA encoding nucleotides 382-627 of exon 3 through exon 5 including a translational start codon were amplified by PCR for HB-EGF$_{\Delta N}$ and HB-EGF$_{\Delta C}$, respectively. PCR reactions were performed in a final volume of 20 µl containing 4 ng/µl of HB-EGF cDNA, 0.5 µl forward and reverse primers (10 µM), 2.0 µl of 10× reaction buffer, 0.5 µl dNTPs, and 0.5 µl Taq polymerase (New England Biolabs: Beverly, Mass.). Each reaction was subjected to 94° C. (5 min), 35 cycles of 94° C. (30 s), 57° C. (1 min), and 72° C. (40 s), followed by an extension at 72° C. (10 min). Reaction products were separated by 1.0% agarose gel electrophoresis, purified by gel extraction kit (QIAGEN), HB-EGF$_{\Delta N}$ was cloned into the plasmid vector pcDNA 3.1/V5-His TOPO (Invitrogen), while HB-EGF$_{\Delta C}$ was cloned into pEF6-V5-His. Both strands of each HB-EGF construct were sequenced using ABI 3730 Genetic Analyzer. Following are the primers for generating HB-EGF$_{\Delta N}$ and HB-EGF$_{\Delta C}$ variants:

| Gene | Forward and Reverse primers | |
|---|---|---|
| HB-EGF$_{\Delta N}$ | 5'-ATGCGGGCTCCCTCCTGCATC-3 | (SEQ ID NO: 9) |
| | 5'-CAACCCGTACTGATTAAGGGTG-3' | (SEQ ID NO: 10) |
| HB-EGF$_{\Delta C}$ | 5'-ACGTCGCGGATATCATGAAGCTGC-3' | (SEQ ID NO: 11) |
| | 5'-CCTCTCCTTTAGTACCTAAAC-3' | (SEQ ID NO: 12) |

Example 3

Generation of Stable Mammalian Cell Lines Expressing proHB-EGF, ADAM 12, HB-EGF$_{\Delta N}$ or HB-EGF$_{\Delta C}$ In order to determine whether the soluble, mature form of HB-EGF and/or HB-EGF C is responsible for stimulation of adipogenesis, cDNA constructs were cloned in which one lacks a functional, soluble, mature HB-EGF capable of binding to EGFRs, termed HB-EGF$_{\Delta N}$ yet maintaining the ectodomain processing site by ADAMs at Pro148-Val149. Nanba et al., Cytokine Growth Factor Rev., 15, 15-19 (2004). The second HB-EGF cDNA construct lacks a functional HB-EGF C domain, yet maintains the minimal amount of intracellular domain necessary for processing, termed HB-EGF$_{\Delta C}$. Nanba et al., J. Cell Biol., 163, 489-502 (2003) ADAM 12S and either HB-EGF$_{\Delta N}$ or HB-EGF$_{\Delta C}$ were stably co-expressed in mouse fibroblasts.

Mouse fibroblasts or human epidermoid carcinoma (A431) cells were maintained in DMEM (Cellgro, Herndon, Va.) supplemented with 10% fetal bovine serum, penicillin (100 U/ml) and streptomycin (100 µg/ml) (BioWhitaker, Walkersville, Md.). Upon growing to 90% confluence, the cells were transfected with or without (mock transfection) plasmids (10.0 µg/ml) encoding proHB-EGF, ADAM 12S, HB-EG-F$_{AN}$, or HB-EGF$_{AC}$ using Lipofectamine™ 2000 (Invitrogen, Carlsbad, Calif.), according to the manufacturer's recommendations. 48 hours post-transfection, cells were treated with G418 (1.0 mg/ml, Invitrogen) for pcDNA3.1 vector and blasticidin (10 µg/ml) for pEF6-V5 His vector and propagated. The two vectors are show in FIG. 5. In order to generate a stable cell line co-expressing ADAM 12S and either proHB-EGF, HB-EGF$_{AN}$, or HB-EGF$_{AC}$, 10.0 µg/ml of pEF6/V5-His: ADAM 12S was transfected proHB-EGF, or HB-EGF$_{AN}$ or HB-EGF$_{AC}$ stable cell lines using Lipofectamine™ 2000 (Invitrogen, Carlsbad, Calif.). Stably transfected ADAM 12S cells were screened by blasticidin (10.0 µg/ml, Invitrogen) 48 h post-transfection, while stably co-expression cell lines were generated using antibiotics both G418 (1.0 mg/ml, Invitrogen) and blasticidin (10.0 µg/ml, Invitrogen).

Figure 6:
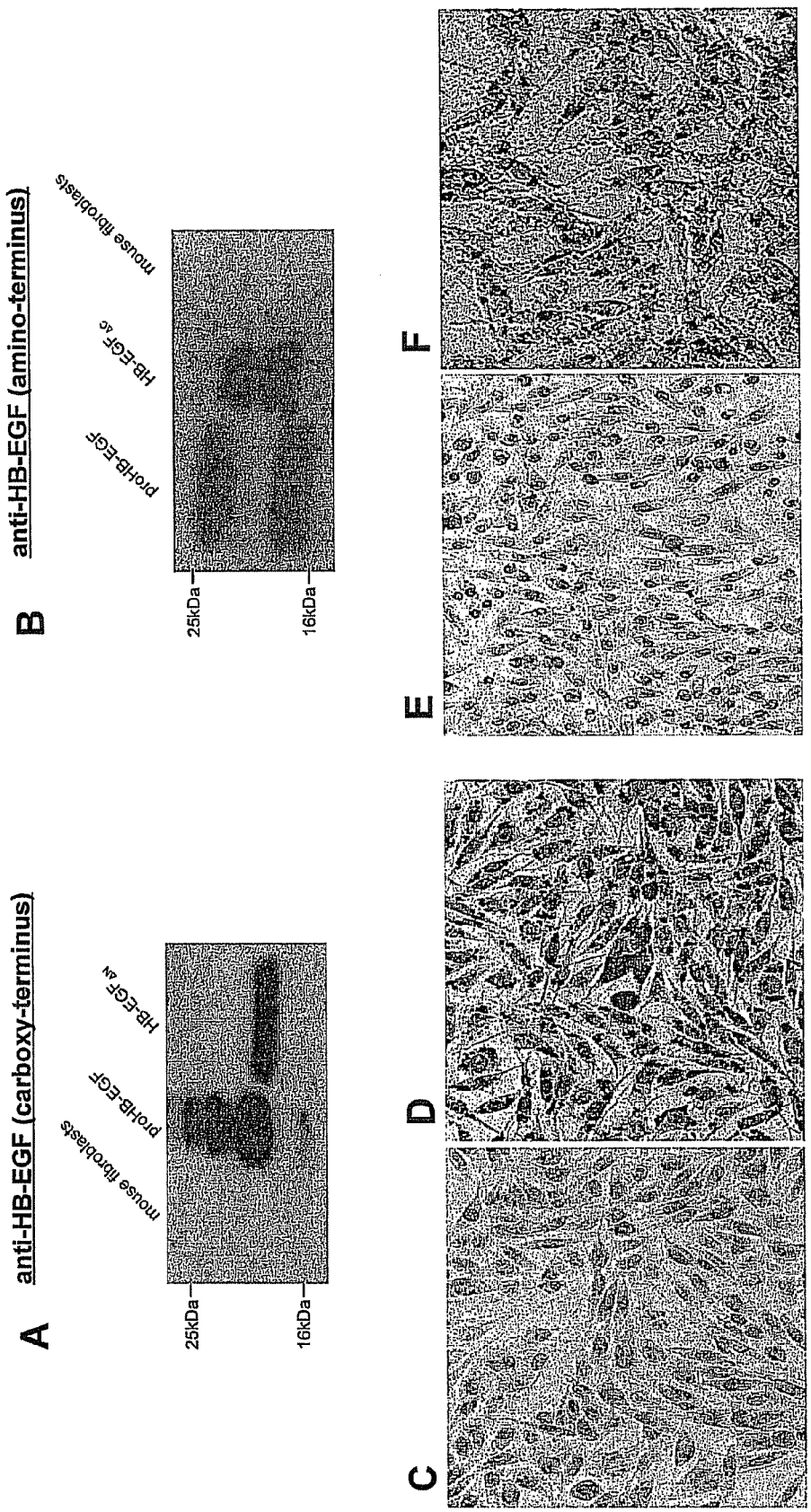
FIG. 6 shows the western blot analysis of HB-EGF$_{AN}$ and HB-EGF$_{AC}$ in panels A and B, respectively. Panels C, D, E, and F show stable modified fibroblasts subjected to Oil Red O staining.

HB-EGF proteins were identified by western analysis using either HB-EGF C anti-sera or an amino terminal anti-HB-EGF antibody and resulted in an 18 kDa HB-EGF immunoreactive protein from HB-EGF$_{AN}$ cells (FIG. 6, panel A), whereas HB-EGF immunoreactive proteins of 18 kD and 20 kDa, proteins were identified from HB-EGF$_{AC}$ stable cell lines (FIG. 6, panel B). Immunoreactive proteins of 6.5 kDa, 21 kDa, and 24 kDa were observed from proHB-EGF expressing cells (FIG. 6, panels A and B). HB-EGF$_{AN}$ or HB-EGF$_{AC}$ stable cell lines lacked Oil Red O staining, suggesting that these recombinant HB-EGF proteins are not sufficient to stimulate adipogenesis (FIG. 6, panels C and E, respectively). Interestingly, mouse fibroblasts that co-express ADAM 12S and either HB-EGF$_{AN}$ or HB-EGF$_{AC}$ stimulated adipogenesis, as identified by Oil Red O staining (FIG. 6, panel D and F, respectively). These results suggest that both soluble, mature HB-EGF and HB-EGF C are each capable of stimulating adipogenesis.

Example 4

Preparation of Cell Lysates for Western Blots

Stable cell lines were grown in 100 mm culture dishes (Corning), washed with PBS three times, on ice and suspended in ice-cold cell lysis buffer (1 mM sodium phosphate, 1 mM EDTA, and 1 mM Tris-HCl, pH 7.4) for 10 min. The cells were scraped from dishes, centrifuged at 13×1000 g for 15 min at 4° C. and stored at −80° C. Total cellular protein was extracted from cells lysed by brief sonication in cell lysis buffer and protein concentration determined using BCA protein assay kit (Pierce). 20 µg total protein was separated on 12% sodium dodecyl sulfate polyacrylamide gel electrophoresis (SDS-PAGE) under reducing conditions and transferred to PVDF membrane (Millipore). Membranes were blocked with TBST (0.1% Tween, Fisher) plus 5% non-fat dry milk overnight at 4° C. with gentle agitation, washed with TBST (0.1% Tween) three times (15 min each), and incubated with primary antibody overnight at 4° C. (e.g., rabbit HB-EGF C anti-sera, 1:200; goat anti the N-terminal portion of human HB-EGF, 1:200, R&D System), followed by incubation with HRP-conjugated secondary antibodies for 1 hour at room temperature (goat anti-rabbit IgG; rabbit anti-goat IgG, Jackson ImmunoResearch Laboratories). Immunoreactive proteins were visualized by application of West Pico Chemiluminescent SuperSignal kit (Pierce) and developed on film.

Figure 7:
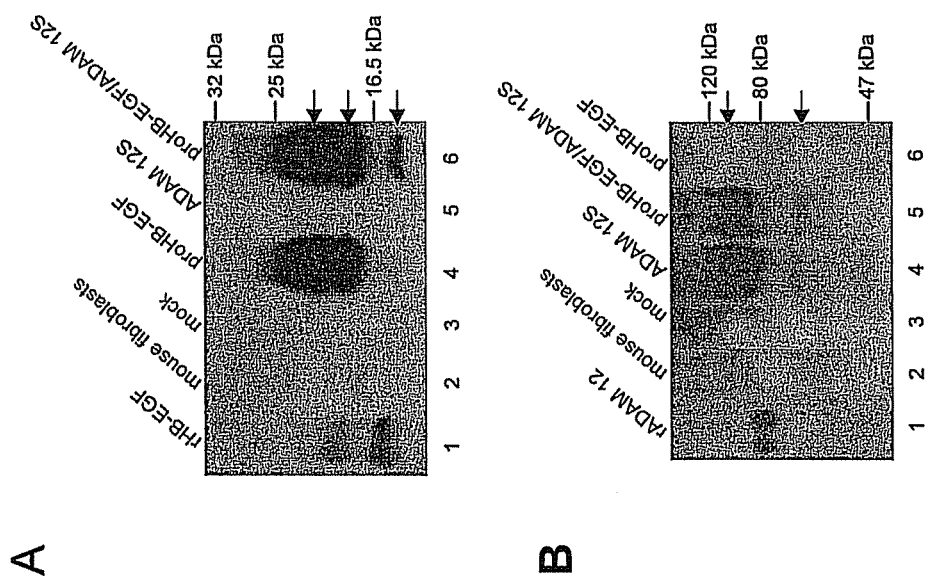
FIG. 7 shows the results of western blot analysis using antibodies to the specific proteins and horseradish peroxidase (HRP)-conjugated secondary antibodies. Panel A shows the results for HB-EGF and panel B shows the results for ADAM 12.

To demonstrate that recombinant hHB-EGF or ADAM 12S was synthesized in stable cell lines transfected with either pcDNA3.1hHB-EGF-TOPO, pcDNA3.1-TOPO, pEF6/ADAM 12S-V5 His-TOPO or pcDNA3.1hHB-EGF-TOPO and pEF6/ADAM 12S-V5 His-TOPO, cellular lysates were analyzed using an anti-hHB-EGF antibody (R&D Systems) or anti-human ADAM 12 antibody (R&D Systems). HB-EGF immunoreactive proteins of 12 kDa, 21 kDa, and 24 kDa were identified in pcDNA3.1hHB-EGF-TOPO and pcDNA3.1hHB-EGF-TOPO/pEF6/ADAM 12S-V5 His-TOPO co-expressing cells, representing mature soluble hHB-EGF and two membrane bound forms of HB-EGF, respectively (FIG. 7A, lanes 4 and 6). No immunoreactive HB-EGF proteins were observed in mouse fibroblasts, pcDNA3.1-TOPO or pEF6/ADAM 12S-V5 His-TOPO expressing cell lines (FIG. 7A, lanes 2, 3, 5). Recombinant hHB-EGF (R&D Systems) was used as a positive control (FIG. 7A, lane 1). Furthermore, immunoreactive ADAM 12S proteins of 68 kDa and 92 kDa were observed in pEF6/ADAM 12S-V5 His-TOPO and pcDNA3.1hHB-EGF-TOPO/pEF6/ADAM 12S-V5 His-TOPO co-expressing cells (FIG. 7B, lanes 4 and 5). No ADAM 12S immunoreactive proteins were observed in mouse fibroblasts, pcDNA3.1-TOPO, or pcDNA3.1hHB-EGF-TOPO stable cell lines (FIG. 7B, lanes 2, 3, 6). Recombinant ADAM 12S (R&D Systems) was used as a positive control (FIG. 7B, lane 1).

Example 5

Oil Red O Staining of Lipid Droplets of Cultured Cells

Cells were grown in the 60 mm culture dishes (Corning). After reaching a cell confluence of 50-70%, the cells were washed with 1.0 ml of PBS for three times, fixed with 1.0 ml of 10% formalin for 60 minutes at room temperature. Oil Red O stock stain solution was prepared by mixing 0.3 g oil red O in 100 ml of isopropanol overnight at room temperature and filtered by using Whatman #2 filter papers. The formalin was removed and the cells were washed with deionized water. The culture dishes were aspirated and added with 1.0 ml of 60% isopropanol working solution to incubate 5 minutes at room temperature. Oil Red O working solution was prepared by diluting 30 ml of the stock stain with 20 ml of distilled water, filtered with Whatman #1 filter papers into a Coplin jar, and covered with a lid immediately. The 60% working isopropanol was removed and the culture dishes were filled with 1.0 ml working solution of Oil Red O, incubated for 5 minutes at room temperature. The cells were rinsed with deionized water until fluid becomes clear, and counterstained with 1 ml of hematoxylin for 1 minute at room temperature. The hematoxylin was then removed from the wells, and the cells were rinsed with deionized water and imaged under a microscope (Olympus).

Oil Red O staining was used to demonstrate the effect of combining HB-EGF and ADAM 12S in a stable fibroblast cell line. Co-expression of pcDNA3.1 hHB-EGF-TOPO and pEF6/ADAM 12S-V5 His-TOPO in mouse fibroblasts exhibited an unexpected finding in which oil droplets appear after approximately 3 weeks expression of HB-EGF and ADAM 12S, that stimulates ectodomain shedding of the membrane-bound HB-EGF. No oil droplets were observed in pcDNA3.1-TOPO, pcDNA3.1hHB-EGF-TOPO, or pEF6/ADAM 12S-V5 His-TOPO stable cell lines. These results indicate that co-expression of HB-EGF and ADAM 12S stimulate adipogenesis in mouse fibroblasts. In order to confirm that HB-EGF and ADAM 12S co-expressing cells stimulate adipogenesis, the inventors stained all stable cell lines with Oil Red O, a fat soluble dye, to detect lipids. Mouse fibroblasts that co-express HB-EGF and ADAM 12S exhibited oil red o staining, while mouse fibroblasts, pcDNA3.1-TOPO, pcDNA3.1hHB-EGF-TOPO, and pEF6/ADAM 12S-V5 His-TOPO stable cell lines lacked Oil Red O staining.

In addition, to address whether proHB-EGF and ADAM 12S stimulation of adipogenesis is restricted to mouse fibroblasts, a human epidermoid carcinoma (A431) cell line was used to recapitulate adipogenesis by proHB-EGF and ADAM 12S coexpression. Similar to mouse fibroblasts, A431 cells, mock-transfected, proHB-EGF, or ADAM 12S stably expressing cell lines failed to stimulate adipogenesis when stained with Oil Red O. Conversely, stable expression of proHB-EGF and ADAM 12S were positive for Oil Red O staining.

The inventors also examined if adipogenesis can be inhibited by incubation of HB-EGF and ADAM 12S co-expressing cells with the matrix metalloprotease inhibitor KB-R7785 (20 µM) added to the culture media. HB-EGF and ADAM 12S co-expressing cells that are positive for Oil Red O staining lack Oil Red O staining after 3 weeks incubation with KB-R7785. These results suggest that processing of pro-HB-EGF is absolutely required for HB-EGF to stimulate adipogenesis.

Example 6

Analysis of Cell Proliferation Rate

Cells growing in 48-well plate (Fisher) were cultured with growth media (DMEM supplemented with 1% penicillin/streptomycin and 10% FBS) containing 5-bromo-2-deoxyuridine (BrdU, 20 µM, Sigma) in an incubator at 37° C. for 18 hours, fixed with 4% paraformaldehyde for 30 min at 4° C., and washed in 0.1 M PBS (pH 7.4) with 1% Triton X100. Each well was incubated in HCl (1N) for 10 min on ice to break open the DNA structure of the cells, followed by HCl (2N) for 5 min at room temperature. The cells in each well were then washed in PBST (1% Triton X100, pH 7.4) and incubated in PBST (1% Triton X100, pH 7.4) containing 10% normal goat serum (Sigma) for one hour at room temperature prior to incubating overnight at 4° C. with rat anti-BrdU antibodies (1:50, Santa Cruz Biotechnology). The cells were subsequently washed with PBST (1% Triton X100, pH 7.4), incubated with secondary antibodies fluorescein (FITC)-conjugated goat anti-rat (1:100, Jackson ImmunoResearch Laboratories) for one hour at room temperature, and stained with DAPI dissolved in PBS for 10 minutes. The BrdU positive (proliferating) cells were imaged under Olympus FV500 laser scanning confocal microscope.

Using the described methods, the inventors determined the cellular proliferation properties of each stable cell line. BrdU positive cells were identified in mouse fibroblasts, mock-transfected, proHB-EGF, and ADAM 12 stable cell lines. However, no BrdU positive cells (FITC) were detected in proHB-EGF/ADAM 12S expressing cells that exhibit adipogenesis. Nuclei of each stable cell line are identified with DAPI stain and FITC and DAPI merged to demonstrate BrdU nuclear incorporation.

Example 7

Inhibition of Adipogenesis by KB-R7785 and Neutralizing Anti HB-EGF Antibody

KB-R7785 ([4-(N-hydroxyamino)-2R-isobutyl-3S-methylsuccinyl]-L-phenylglycine-N-methylamide), a metalloprotease inhibitor that suppresses the shedding of HB-EGF by directly binding to ADAM 12, was applied to the growth media (DMEM plus 1% penicillin/streptomycin and 10% FBS) of stable cell lines co-expressing HB-EGF-ΔC and ADAM 12S at a working concentration of 10 µM for 4 weeks. Neutralizing anti-human HB-EGF antibody (R and D Systems), which selectively recognizes the processed, mature form of HB-EGF, was added to the culture media (DMEM plus 1% penicillin/streptomycin and 10% FBS) of stable cell lines co-expressing HB-EGF and ADAM 12S at a working concentration of 10 µg/mL for 4 weeks. Both stable cell lines were then stained with Oil Red O (Allied Chemical Corporation, New York, N.Y.) as described in Example 5 to identify whether both KB-R7785 and neutralizing anti-human HB-EGF antibody are able to inhibit the adipogenesis. The KB-R7785 in this study was offered cordially by Shigeki Higashiyama (Ehime University School of Medicine and Ehime University Hospital).

Subsequent to transdifferentiation of mouse fibroblasts stably transfected with ADAM 12S and HB-EGF to brown adipocytes, incubation of these cells with the ADAM 12S inhibitor KB-R7785 [10 µM] returned the brown adipocytes to mouse fibroblasts over 4 weeks and lacked adipocyte morphology.

Example 8

Immunocytochemical Localization of HB-EGF-C

Cells growing in 48-well plate (Fisher) were fixed with 4% (w/v) paraformaldehyde (PFA) for 15 minutes, permeabilized with PBST (1% Triton-X-100) for 10 minutes at room temperature, and blocked with 5% goat serum RT in PBST (1% Triton-X-100) for one hour at room temperature. The cells were then incubated with primary antibody rabbit anti HB-EGF-C (diluted at 1:100; Santa Cruz Biotechnology) overnight at 4° C. Following extensive washing steps, the cells were incubated with secondary antibody fluorescein (FITC)-conjugated goat anti rabbit (1:100, Jackson ImmunoResearch Laboratories) in 0.1 M PBS. The cells were stained with DAPI and imaged under a fluorescence microscope (Olympus).

HB-EGF, initially synthesized as a membrane bound protein, undergoes extensive proteolytic processing which includes ectodomain shedding by furin (Nakagawa et al., J Biol Chem., 271, 30858-63 (1996)) and ADAM 9, 10, 17 or ADAM 12 (Asakura et al., Nat. Med., 8, 35-40 (2002), yielding a soluble, mature form of HB-EGF capable of binding and activating EGF receptors (EGFR). Following ectodomain shedding is processing, the intracellular domain is processed by an unidentified mechanism resulting in a carboxy-terminal domain of HB-EGF (HB-EGF C).

The inventors wanted to demonstrate that HB-EGF C migrates to the nucleus upon proteolytic processing by ADAM 12S as previously described. An immunohistochemical approach was taken by incubating HB-EGF C anti-sera on pcDNA3.1hHB-EGF-TOPO, pcDNA3.1-TOPO, pEF6/ADAM 12S-V5 His-TOPO or pcDNA3.1hHB-EGF-TOPO and pEF6/ADAM 12S-V5 His-TOPO stable cell lines. pcDNA3.1hHB-EGF-TOPO stable cell lines express the full-length HB-EGF cDNA encoding proHB-EGF and resulted in a ubiquitous pattern of expression. pcDNA3.1hHB-EGF-TOPO and pEF6/ADAM 12S-V5 His-TOPO stable cell lines, which express proHB-EGF and ADAM 12S protease also resulted in ubiquitous HB-EGF expression with a very intense HB-EGF C signal localized in the nucleus. No HB-EGF C immunohistochemical detection was observed in pcDNA3.1-TOPO (mock transfected stable cell lines) or pEF6/ADAM 12S-V5 His-TOPO (ADAM 12S) stable cell lines.

Example 9

Immuncytochemical Analysis of Mitochondria of Cells Co-Expressing HB-EGF and ADAM 12S MitoTracker® Deep Red 633 (Invitrogen) is a far red-fluorescent dye which is able to stain the mitochondria in live cells and the accumulation of the dye is dependent on cell membrane potential. To prepare a stock solution of the dye, the lyophilized MitoTracker® product was dissolved in high-quality anhydrous dimethylsulfoxide (DMSO), making a final concentration of 1 mM. The dye is well-retained after fixation. Cells were grown on coverslips inside a culture dish (Corning) filled with Dulbecco's modified Eagle's media plus 10% FBS (DMEM, Invitrogen). After reaching a cell confluency of 50-70%, cells were treated with MitoTracker Deep Red 633 at a working concentration of 100-500 nM for one hour, washed with PBS and fixed with 4% paraformaldehyde, permeabilized with PBST [1% Triton X-100: $C_{14}H_{22}O(C_2H_4O)_n$), Fisher]. The cells were subsequently labeled with the DAPI. Images were recorded with a 100× oil immersion objective under Olympus FV500 laser scanning confocal microscope.

Example 10

Co-Expression of ADAM 12S and HB-EGF Stimulates Adipogenesis

To help reveal the molecular and cellular basis of obesity, the inventors investigated the role of ADAM 12 (A Disintegrin And Metalloprotease 12) and HB-EGF (Heparin Binding EGF-like Growth Factor) in adipogenesis.

Individual proHB-EGF stable cell line and ADAM 12S stable cell line did not exhibit adipogenesis when stained with Oil Red O. Interestingly, after culturing the individual proHB-EGF stable cell line and ADAM 12S stable cell line together for 3 weeks, the cells exhibited adipogenesis, as evidenced by Oil Red O staining. This suggests that the ADAM 12S stable cell line and its secreted ADAM 12S likely processed the membrane bound proHB-EGF of the proHB-EGF stable cell line resulting in adipogenesis. Furthermore, application of the culture media from ADAM 12S expressing stable cell line added to the proHB-EGF stable cell line also resulted in adipogenesis, further supporting the hypothesis that the secreted form of ADAM 12S stimulates adipogenesis via proHB-EG Stimulation of adipogenesis was performed using cultured mouse fibroblasts and human epidermoid carcinoma (A431) cells stably transfected with human HB-EGF and ADAM 12S cDNAs, as described in Examples 1 and 3. Stable cell lines were examined for expression of recombinant ADAM 12S protein (68 kDa and 92 kDa) and HB-EGF proteins (6.5, 20, and 22 kDa) by western blot analysis using ADAM 12S specific antibody and HB-EGF antisera that specifically recognizes the intracellular domain of HB-EGF, as described in Example 4. Stable expression of either ADAM 12S or HB-EGF cDNA did not affect fibroblast morphology; however, stable co-expression of both ADAM 12S and HB-EGF cDNAs in fibroblasts stimulated significant fat deposition (adipogenesis), as demonstrated by the method of Example 5. Furthermore, co-expression of ADAM 12S and HB-EGF significantly slowed cell growth as compared to ADAM 12S or HB-EGF expressing cells, as described in Example 6.

Inhibition of sHB-EGF binding to EGF receptors using a neutralizing antibody or the inhibition of ectodomain shedding of HB-EGF metalloproteinase inhibitor KB-R7785 indicated that adipogenesis can be mediated by HB-EGF-C, as shown in Example 7. Furthermore, immunocytochemistry revealed that HB-EGF-C was translocated to the nucleus, as shown in Example 8. Further immunocytochemical analysis demonstrated that co-expression of HB-EGF and ADAM 12S alter the morphology of the mitochondria of the modified cells, as shown in Example 9. Expression of an HB-EGF cDNA lacking the intracellular domain, termed HB-EGF C, stimulated adipogenesis. Together, these data indicate that ADAM 12S bioactivity is required for adipogenesis in an HB-EGF dependent manner, and that both sHB-EGF and HB-EGF-C, which was prepared using the deletion mutant HB-EGF$_{\Delta C}$ described in Example 2, stimulated adipogenesis independently.

Example 11

Quantitative Real-Time RT-PCR

In order determine whether the Oil Red O positive cells in our HB-EGF/ADAM 12S expressing cells are white adipose tissue (WAT) or brown adipose tissue (BAT), the inventors employed a quantitative real-time RT-PCR approach for proteins involved in the WAT pathway including peroxisome proliferator-activated receptor gamma (PPARγ), CCAAT/enhancer binding protein alpha (C/EBPα), and serine-threonine protein kinase (AKT-1) as well as transcription factors involved in the BAT pathway including the proteins PRDM16, peroxisome proliferator-activated receptor gamma coactivator 1 alpha (PGC-1$_\alpha$) and uncoupling protein 1 (UCP-1).

A one-step real time RT-PCR Green SYBR kit (QuantiTect) was used to perform real time RT-PCR in Rotor Gene 300, according to the manufacturer's protocols (Rotor-Gene™ produced by Corbett Research, Australia). Total RNA was extracted from mouse fibroblasts with TriReagent (Molecular Research Center, Cincinnati, Ohio), DNase-digested. A typical reaction mixture contained 200 ng total RNA, with the final concentration of primers being 0.5 μM, and the final concentration of Mix SYBR being 0.2 μM. The cycles were 55° C. for 30 min, 95° C. for 30 sec, 95° C. for 15 sec, 55° C. for 15 sec, 72° C. for 30 sec. A total of 45 cycles were used in the amplification. Relative quantification of the gene expression by real-time RT-PCR was based on the mathematic model developed by Pfaffl. The primer sets for the target genes and internal control are:

| Genes | Forward and Reverse primers | |
|---|---|---|
| PRDM16 | 5'-GAATGGACAAACGGCCT-3' | (SEQ ID NO: 13) |
| | 5'-TCTACGTCCTCTGGCTTTG-3' | (SEQ ID NO: 14) |
| PGC-1 alpha | 5'-ACC CCA GAG TCA CCA AAT-3' | (SEQ ID NO: 15) |
| | 5'-CAC ACT TAA GGT TCG CTC A-3' | (SEQ ID NO: 16) |
| UCP-1 | 5'-TCTTCAGGGAGAGAAACACC-3' | (SEQ ID NO: 17) |
| | 5'-AATGAACACTGCCACACC-3' | (SEQ ID NO: 18) |
| PPAR-γ | 5'-CCACAGTTGATTTCTCCAGC-3' | (SEQ ID NO: 19) |
| | 5'-GCAGGTTCTACTTTGATCGC-3' | (SEQ ID NO: 20) |
| C/EBP | 5'-GGACAAGAACAGCAACGA-3' | (SEQ ID NO: 21) |
| | 5'-TCAACTCCAGCACCTTCT-3' | (SEQ ID NO: 22) |
| AKT-1 | 5'-TCCTCAAGAACGATGGCA-3' | (SEQ ID NO: 23) |
| | 5'-ACTCTCGCTGATCCACAT-3' | (SEQ ID NO: 24) |

-continued

| Genes | Forward and Reverse primers |
|---|---|
| GAPDH | 5'-TTG TGG AAG GGC TCA TGA-3' (SEQ ID NO: 25)<br>5'-CAT CACGCC ACA GCT TT-3' (SEQ ID NO: 26) |

No significant differences in PPARγ, C/EBPα, or AKT-1 mRNAs were found in all stable cell lines examined, but they were upregulated in WAT 13-, 400- and 3.5-fold, respectively (FIG. 8, panels A-C). PRDM16 mRNA levels were significantly upregulated 12-fold in HB-EGF/ADAM 12S co-expressing cells and 138-fold in BAT compared to mouse fibroblasts, mock-transfected, proHB-EGF, and ADAM 12S cell lines (FIG. 8, panel D). PGC-1α mRNA was significantly upregulated 38-fold in HB-EGF/ADAM 12S co-expressing cells compared to other cell lines (FIG. 8, panel E). Finally, UCP-1 mRNA was significantly upregulated 5-fold and 7,322-fold in HB-EGF/ADAM 12S co-expressing cells and BAT, respectively (FIG. 8, panel F). These results indicate that HB-EGF and ADAM 12S co-expression stimulate adipogenesis utilizing the BAT molecular pathway.

The complete disclosure of all patents, patent applications, and publications, and electronically available materials cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A method for converting animal cells into brown adipose tissue cells, comprising
transforming the animal cells using an expression vector comprising a nucleotide sequence encoding HB-EGF operatively linked to a promoter and a nucleotide sequence encoding ADAM 12 operatively linked to a promoter;
wherein the animal cells are converted in vitro.

2. The method of claim 1, wherein the ADAM 12 is ADAM 12S.

3. The method of claim 1, wherein the nucleotide sequence encoding HB-EGF consists of a nucleotide sequence substantially similar to SEQ ID NO: 3 and the nucleotide sequence encoding ADAM 12 consists of a nucleotide sequence substantially similar to SEQ ID NO: 4.

4. The method of claim 1, wherein the expression vector is a plasmid.

5. The method of claim 1, wherein the expression vector is a viral vector.

6. The method of claim 5, wherein the expression vector is a lentiviral vector or an adenoviral vector.

7. The method of claim 1, wherein the expression vector is targeted to animal cells of a particular tissue.

8. The method of claim 7, wherein at least one of the promoters is a promoter found in a target cell type in the particular tissue.

9. The method of claim 8, wherein the target cell type is a white adipose cell.

* * * * *